US008968782B2

(12) United States Patent
Chappa et al.

(10) Patent No.: US 8,968,782 B2
(45) Date of Patent: Mar. 3, 2015

(54) COMBINATION DEGRADABLE AND NON-DEGRADABLE MATRICES FOR ACTIVE AGENT DELIVERY

(75) Inventors: Ralph A. Chappa, Prior Lake, MN (US); Robert W. Hergenrother, Eden Prairie, MN (US); Paula Bushendorf, Brooklyn Park, MN (US); Joram Slager, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 977 days.

(21) Appl. No.: 11/770,316

(22) Filed: Jun. 28, 2007

(65) Prior Publication Data
US 2008/0020045 A1 Jan. 24, 2008

Related U.S. Application Data

(60) Provisional application No. 60/806,043, filed on Jun. 28, 2006.

(51) Int. Cl.
*A61K 47/30* (2006.01)
*A61K 38/02* (2006.01)
(Continued)

(52) U.S. Cl.
CPC .............. *A61L 27/58* (2013.01); *A61L 27/48* (2013.01); *A61L 27/54* (2013.01); *C08L 23/0853* (2013.01);
(Continued)

(58) Field of Classification Search
USPC ............ 424/486, 130.1, 423, 426; 514/772.3
See application file for complete search history.

(56) References Cited

U.S. PATENT DOCUMENTS

| 4,027,676 A | * | 6/1977 | Mattei ........................... 606/230 |
| 4,507,411 A | * | 3/1985 | Gordon et al. ................ 523/436 |

(Continued)

FOREIGN PATENT DOCUMENTS

| WO | WO-97/25979 | 7/1997 |
| WO | WO-00/74655 | 12/2000 |

(Continued)

OTHER PUBLICATIONS

Mara Lovrecich and Fulvio Rubessa, "Morphology and Surface Properties of Blends of Eudragit RS with Different Poly(ethylene Glycol)s", Pharmaceutical Development and Technology, 3(1), 123-129 (1998).*

(Continued)

*Primary Examiner* — Ernst V Arnold
*Assistant Examiner* — Hong Yu
(74) *Attorney, Agent, or Firm* — Pauly, DeVries Smith & Deffner, LLC

(57) ABSTRACT

The present invention relates to relates to combination degradable and non-degradable matrices and related methods. In an embodiment, the invention includes an active agent delivery matrix including a degradable polymer network, a non-degradable polymer network, the non-degradable polymer network interspersed within the degradable polymer network, and an active agent. In an embodiment, the invention includes an active agent elution control matrix including a degradable polymer; and a non-degradable polymer interspersed with the degradable polymer. In an embodiment, the invention includes a method of making an active agent delivery matrix including mixing a degradable polymer with a first solvent to form a degradable polymer solution; mixing a non-degradable polymer with a second solvent to form a non-degradable polymer solution; and simultaneously depositing the degradable polymer solution and the non-degradable polymer solution onto a substrate.

3 Claims, 14 Drawing Sheets

(51) Int. Cl.
*A61K 9/00* (2006.01)
*A61K 39/395* (2006.01)
*A61K 45/00* (2006.01)
*A61L 27/58* (2006.01)
*A61L 27/48* (2006.01)
*A61L 27/54* (2006.01)
*C08L 23/08* (2006.01)
*C08L 33/08* (2006.01)
*C08L 71/02* (2006.01)

(52) U.S. Cl.
CPC ...... *A61L 2300/252* (2013.01); *A61L 2300/256* (2013.01); *A61L 2300/604* (2013.01); *C08L 23/0869* (2013.01); *C08L 33/08* (2013.01); *C08L 71/02* (2013.01); *C08L 2201/06* (2013.01)
USPC ........ 424/486; 424/130.1; 424/426; 424/423; 514/772.3

(56) References Cited

U.S. PATENT DOCUMENTS

| | | | |
|---|---|---|---|
| 4,638,045 | A | 1/1987 | Kohn et al. |
| 5,466,233 | A | 11/1995 | Weiner et al. |
| 6,214,901 | B1 | 4/2001 | Chudzik et al. |
| 6,303,148 | B1 | 10/2001 | Hennink et al. |
| 6,395,302 | B1 | 5/2002 | Hennink et al. |
| 6,719,750 | B2 | 4/2004 | Varner et al. |
| 2001/0001658 | A1* | 5/2001 | Chen et al. ............ 424/49 |
| 2003/0014036 | A1 | 1/2003 | Varner et al. |
| 2004/0133155 | A1 | 7/2004 | Verner et al. |
| 2004/0224001 | A1* | 11/2004 | Pacetti et al. ............ 424/423 |
| 2005/0019371 | A1 | 1/2005 | Anderson et al. |
| 2005/0059956 | A1 | 3/2005 | Varner et al. |
| 2005/0084536 | A1* | 4/2005 | Van Buitenen et al. ....... 424/489 |
| 2005/0119723 | A1 | 6/2005 | Peacock, III |
| 2005/0143363 | A1 | 6/2005 | De Juan et al. |
| 2005/0196422 | A1 | 9/2005 | Hossainy et al. |
| 2005/0255142 | A1* | 11/2005 | Chudzik et al. ............ 424/426 |
| 2005/0271703 | A1 | 12/2005 | Anderson et al. |
| 2005/0271706 | A1 | 12/2005 | Anderson et al. |
| 2005/0276837 | A1 | 12/2005 | Anderson et al. |
| 2005/0281863 | A1 | 12/2005 | Anderson et al. |
| 2005/0287188 | A1 | 12/2005 | Anderson et al. |
| 2006/0110428 | A1 | 5/2006 | deJuan et al. |
| 2007/0026037 | A1 | 2/2007 | Kloke et al. |
| 2007/0065481 | A1 | 3/2007 | Chudzik et al. |
| 2007/0110787 | A1* | 5/2007 | Hossainy et al. ............ 424/424 |
| 2007/0128343 | A1 | 6/2007 | Chappa |
| 2007/0218102 | A1 | 9/2007 | Chudzik et al. |
| 2007/0224247 | A1 | 9/2007 | Chudzik et al. |
| 2007/0260054 | A1 | 11/2007 | Chudzik |

FOREIGN PATENT DOCUMENTS

| | | |
|---|---|---|
| WO | WO-2007/016405 | 2/2007 |
| WO | WO-2007/059144 | 5/2007 |
| WO | WO-2007/109069 | 9/2007 |

OTHER PUBLICATIONS

"PCT International Search Report and Written Opinion from International Application No. PCT/US2007/072357, pp. 1-13, mailed Dec. 8, 2008".

Banks, Jim et al., "Implants: the Biodegradable Future", *Medical Device Developments* www.mdd-spg.com Feb. 2006 , 35-36.

Ertel, S I. et al., "Evaluation of Poly(DTH carbonate), a Tyrosine-Derived Degradable Polymer, for Orthopedic Applications", *J Biomed Mater Res.* Nov. 1995 , 29(11): 1337-1348.

Yeo, Yoon et al., "A New Microencapsulation Method Using an Ultrasonic Atomizer Based on Interfacial Solvent Exchange", *Journal of Controlled Release* 2004 , 100: 379-388.

Yeo, Yoon et al., "Characterization of Reservoir-Type Microcapsules Made by the Solvent Exchange Method", *AAPS PharmSciTech* Nov. 5, 2004 , 5 (4) Article 52.

Parylene Engineering Brochure, *Parylene Basics*, http://www.paryleneengineering.com/basics_of_parylene.html, 2009, 3 pages.

* cited by examiner

US 8,968,782 B2

COMBINATION DEGRADABLE AND NON-DEGRADABLE MATRICES FOR ACTIVE AGENT DELIVERY

This application claims the benefit of U.S. Provisional Application No. 60/806,043, filed Jun. 28, 2006, the content of which is herein incorporated by reference.

FIELD OF THE INVENTION

The present invention relates to matrices for active agent delivery and related methods. More specifically, the present invention relates to combination degradable and non-degradable matrices and related methods.

BACKGROUND OF THE INVENTION

Therapeutic benefits can be achieved in some instances by providing an active agent to a specific, localized target tissue, instead of systemically. In this manner, the effect of the agent on the target tissue can be maximized while limiting side effects on other tissues. Therapeutic benefits can also be achieved by providing an active agent to a subject in a manner that provides controlled release of the active agent.

One approach to providing these benefits is to use a degradable matrix which retains an active agent before releasing it as the degradable matrix breaks down. Degradable matrices offer the advantage of being able to control the release rate of active agents that do not readily diffuse through non-degradable coatings. However, some types of degradable matrices may lack sufficient structural integrity and may develop structural defects such as cracks and gaps. In some cases, the lack of structural integrity can lead to portions of the matrix detaching from and falling off the substrate it is disposed on. As a result, degradable matrices may be unsuitable for use with some types of medical devices.

Accordingly, a need remains for active agent delivery and/or elution control matrices that can be used with a variety of active agents.

SUMMARY OF THE INVENTION

The present invention includes combination degradable and non-degradable matrices and related methods. In an embodiment, the invention includes an active agent delivery matrix including a degradable polymer network, a non-degradable polymer network, the non-degradable polymer network interspersed within the degradable polymer network, and an active agent.

In an embodiment, the invention includes an active agent elution control matrix including a degradable polymer and a non-degradable polymer interspersed with the degradable polymer.

In an embodiment, the invention includes a method of making an active agent delivery matrix including mixing a degradable polymer with a first solvent to form a degradable polymer solution; mixing a non-degradable polymer with a second solvent to form a non-degradable polymer solution; and simultaneously depositing the degradable polymer solution and the non-degradable polymer solution onto a substrate.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which.

Figure 1:
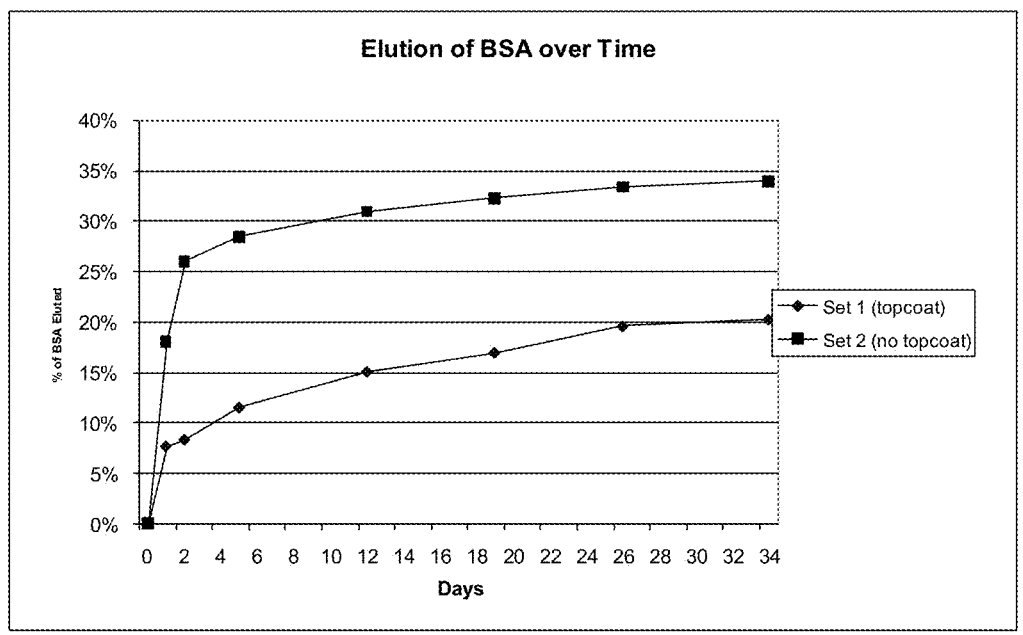
FIG. 1 is a graph showing the elution of BSA from a coating in accordance with an embodiment of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Structural integrity of an active agent delivery and/or elution control coating can be important under some clinical scenarios. Insufficient structural integrity of a coating can lead to portions of the coating breaking off of the device which is generally undesirable. As an example, it may be detrimental to have portions of a coating break off from a medical device that is implanted in a sensitive area, such as intraocularly.

The structural integrity of a coating may be challenged in vivo in various ways. By way of example, some medical devices are implanted for a period of time and then later removed. The process of inserting and removing the device can result in frictional forces sufficient to dislodge portions of the coating if it does not have sufficient structural integrity.

Non-degradable polymer matrices can be useful to provide sufficient structural integrity to a coating. However, non-degradable polymer matrices may not provide desired elution rates with some types of active agents. In addition, the solvents used to apply some types of non-degradable polymer matrices may be incompatible with, or otherwise detrimental to, some types of active agents.

Degradable polymer matrices can be useful to provide desired elution rates in some situations where non-degradable polymer matrices are insufficient. Further, some degradable polymer matrices can be applied with a solvent that is not detrimental to specific active agents. However, degradable polymer matrices frequently have insufficient structural integrity.

Embodiments of the invention include coatings with both degradable and non-degradable matrices in combination. In an embodiment, the invention includes an active agent delivery matrix including a degradable polymer network, a non-degradable polymer network, the non-degradable polymer network interspersed within the degradable polymer network, and an active agent. In an embodiment, the invention includes an active agent elution control matrix including a degradable polymer; and a non-degradable polymer interspersed with the degradable polymer.

Combination degradable/non-degradable matrices can offer various advantages. By way of example, combination degradable/non-degradable matrices of the invention can have structural integrity sufficient to prevent portions of the coating from breaking off under the conditions of use. In some embodiments, combination degradable/non-degradable matrices of the invention can provide desired elution rates for active agents that are not adequately controlled by a non-degradable matrix alone. In some embodiments, combination degradable/non-degradable matrices of the invention can preserve activity of an active agent eluted from the combination degradable/non-degradable matrix.

In some embodiments, the non-degradable polymer can form an open-cell structure. The term "open-cell", as used herein, with reference to matrices shall refer to a porous structure wherein the pores are sufficiently interconnected so as to form irregular or regular channels throughout the three-dimensional matrix. The pores may be unfilled or filled with either a fluid or a solid. Methods of the invention can allow the active agent to be disposed within the pores. As such, in some embodiments, the active agent can be purposefully separated from the non-degradable polymer. This can offer advantages such as where the non-degradable polymer is only soluble in solvents that contribute to denaturing or otherwise damaging the active agent.

The term "degradable" as used herein with reference to polymers, shall refer to those natural or synthetic polymers that break down under physiological conditions into constituent components over a period of time. By way of example, many degradable polymers include hydrolytically unstable linkages in the polymeric backbone. The cleavage of these unstable linkages leads to degradation of the polymer. The terms "erodible", "bioerodible", "biodegradable" and "non-durable" shall be used herein interchangeably with the term "degradable".

The term "interpenetrating matrix" as used herein shall refer to a polymer blend comprising two or more polymer matrices which are at least partially interlaced, but are not covalently bonded to one another.

The term "bonded interpenetrating matrix" as used herein shall refer to a polymer blend comprising two or more polymer matrices which are at least partially interlaced and are covalently bonded to one another.

Non-Degradable Polymers

Embodiments of the invention can include one or more non-degradable (durable) polymers. In an embodiment, the non-degradable polymer includes a plurality of polymers, including a first polymer and a second polymer. When the coating solution contains only one polymer, it can be either a first or second polymer as described herein. As used herein, term "(meth)acrylate" when used in describing polymers shall mean the form including the methyl group (methacrylate) or the form without the methyl group (acrylate).

First polymers of the invention can include a polymer selected from the group consisting of poly(alkyl(meth)acrylates) and poly(aromatic(meth)acrylates), where "(meth)" will be understood by those skilled in the art to include such molecules in either the acrylic and/or methacrylic form (corresponding to the acrylates and/or methacrylates, respectively). An exemplary first polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder). In some embodiments, poly(n-butyl methacrylate) (PBMA) is used with a molecular weight of about 200,000 Daltons to about 300,000 Daltons.

Examples of suitable first polymers also include polymers selected from the group consisting of poly(aryl(meth)acrylates), poly(aralkyl (meth)acrylates), and poly(aryloxyalkyl (meth)acrylates). Such terms are used to describe polymeric structures wherein at least one carbon chain and at least one aromatic ring are combined with acrylic groups, typically esters, to provide a composition. In particular, exemplary polymeric structures include those with aryl groups having from 6 to 16 carbon atoms and with weight average molecular weights from about 50 to about 900 kilodaltons. Suitable poly(aralkyl(meth)acrylates), poly(arylalky(meth)acrylates) or poly(aryloxyalkyl (meth)acrylates) can be made from aromatic esters derived from alcohols also containing aromatic moieties. Examples of poly(aryl(meth)acrylates) include poly(9-anthracenyl methacrylate), poly(chlorophenylacrylate), poly(methacryloxy-2-hydroxybenzophenone), poly (methacryloxybenzotriazole), poly(naphthylacrylate) and -methacrylate), poly(4-nitrophenyl acrylate), poly(pentachloro(bromo, fluoro) acrylate) and -methacrylate), and poly(phenyl acrylate) and -methacrylate). Examples of poly (aralkyl (meth)acrylates) include poly(benzyl acrylate) and -methacrylate), poly(2-phenethyl acrylate) and -methacrylate, and poly(1-pyrenylmethyl methacrylate). Examples of poly(aryloxyalkyl (meth)acrylates) include poly(phenoxyethyl acrylate) and -methacrylate), and poly(polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. pEVA co-polymers with lower percent vinyl acetate become increasingly insoluble in typical solvents, whereas those with higher percent vinyl acetate become increasingly soluble.

An exemplary non-degradable polymer mixture includes mixtures of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating solution of between about 0.05 wt. % and about 99 wt. %. In one embodiment the polymer mixture includes pBMA with a molecular weight of from 100 kilodaltons to 900 kilodaltons and a pEVA copolymer with a vinyl acetate content of from 24 to 36 weight percent. In an embodiment the polymer mixture includes pBMA with a molecular weight of from 200 kilodaltons to 300 kilodaltons and a pEVA copolymer with a vinyl acetate content of from 24 to 36 weight percent. The concentration of the active agent or agents dissolved or suspended in the coating mixture can range from 0.01 to 99 percent, by weight, based on the weight of the final coating material.

Second polymers can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers.

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. Such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl (meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

Non-degradable polymers can also include those described in U.S. Publ. Pat. App. No. 2007/0026037, entitled "DEVICES, ARTICLES, COATINGS, AND METHODS FOR CONTROLLED ACTIVE AGENT RELEASE OR HEMOCOMPATIBILITY", the contents of which is herein incorporated by reference. As a specific example, non-degradable polymers can include random copolymers of butyl methacrylate-co-acrylamido-methyl-propane sulfonate (BMA-AMPS). In some embodiments, the random copolymer can include AMPS in an amount equal to about 0.5 mol. % to about 40 mol.

Non-degradable polymers can include those described in U.S. Pat. No. 6,214,901, entitled "BIOACTIVE AGENT RELEASE COATING", the contents of which is herein incorporated by reference.

Degradable Polymers

Degradable polymers used with embodiments of the invention can include both natural or synthetic polymers. Examples of degradable polymers can include those with hydrolytically unstable linkages in the polymeric backbone. Degradable polymers of the invention can include both those with bulk erosion characteristics and those with surface erosion characteristics.

Synthetic degradable polymers can include: degradable polyesters (such as poly(glycolic acid), poly(lactic acid), poly(lactic-co-glycolic acid), poly(dioxanone), polylactones (e.g., poly(caprolactone)), poly(3-hydroxybutyrate), poly(3-hydroxyvalerate), poly(valerolactone), poly(tartronic acid), poly(B-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; and degradable polyhydroxyalkanoates; and copolymers thereof.

Natural or naturally-based degradable polymers can include polysaccharides and modified polysaccharides such as starch, cellulose, chitin, chitosan, and copolymers thereof.

Specific examples of degradable polymers include poly(ether ester) multiblock copolymers based on poly(ethylene glycol) (PEG) and poly(butylene terephthalate) that can be described by the following general structure:

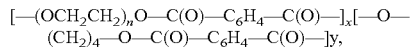

where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. n can be selected such that the molecular weight of the PEG block is between about 300 and about 4000. X and y can be selected so that the multiblock copolymer contains from about 55% up to about 80% PEG by weight. The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure.

Degradable polyesteramides can include those formed from the monomers OH-x-OH, z, and COOH-y-COOH, wherein x is alkyl, y is alkyl, and z is leucine or phenylalanine.

Degradable polymeric materials can also be selected from: (a) non-peptide polyamino polymers; (b) polyiminocarbonates; (c) amino acid-derived polycarbonates and polyarylates; and (d) poly(alkylene oxide) polymers.

In an embodiment, the degradable polymeric material is composed of a non-peptide polyamino acid polymer. Exemplary non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

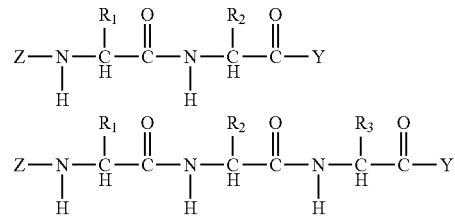

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are degradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, a aminoadipic acid, canavanine, venkolic acid, thiolhistidine, ergothionine, dihydroxyphenylalanine, and other amino acids well recognized and characterized in protein chemistry.

Degradable polymers of the invention can also include polymerized polysaccharides such as those described in U.S. Publ. Pat. Application No. 2005/0255142, entitled "COATINGS FOR MEDICAL ARTICLES INCLUDING NATURAL BIODEGRADABLE POLYSACCHARIDES", U.S. Publ. Pat. Application No. 2007/0065481, entitled "COATINGS INCLUDING NATURAL BIODEGRADABLE POLYSACCHARIDES AND USES THEREOF", and in U.S. Application No. 60/782,957, entitled "HYDROPHOBIC DERIVATIVES OF NATURAL BIODEGRADABLE POLYSACCHARIDES", all of which are herein incorporated by reference.

Degradable polymers of the invention can also include dextran based polymers such as those described in U.S. Pat. No. 6,303,148, entitled "PROCESS FOR THE PREPARATION OF A CONTROLLED RELEASE SYSTEM". Exemplary dextran based degradable polymers including those available commercially under the trade name OCTODEX.

Degradable polymers of the invention can further include collagen/hyaluronic acid polymers.

Degradable polymers of the invention can include multi-block copolymers, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (Tg) of at most 37° C. (Tg) at physiological (body) conditions. The pre-polymers A and B can be a hydrolysable polyester, polyetherester, polycarbonate, polyestercarbonate, polyanhydride or copolymers thereof, derived from cyclic monomers such as lactide (L,D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers can be chosen in such a way that the maximum glass transition temperature of the resulting copolymer is below 37° C. at body conditions. To fulfill the requirement of a Tg below 37° C., some of the above-mentioned monomers or combinations of monomers can be more preferred than others. This may by itself lower the Tg, or the pre-polymer is initiated with a polyethylene glycol with sufficient molecular weight to lower the glass transition temperature of the copolymer. The degradable multi-block copolymers can include hydrolysable sequences being amorphous and the segments can be linked by a multifunctional chain-extender, the segments having different physical and degradation characteristics. For example, a multi-block co-polyester consisting of a glycolide-ε-caprolactone segment and a lactide-glycolide segment can be composed of two different polyester pre-polymers. By controlling the segment monomer composition, segment ratio and length, a variety of polymers with properties that can easily be tuned can be obtained.

Active Agents

Combination degradable/non-degradable coatings of the invention can contain one or more active agents. As used herein, the term "active agent" means a compound that has a particular desired activity. For example, an active agent can be a therapeutic compound that exerts a specific activity on a subject. In some embodiments, active agent will, in turn, refer to a peptide, protein, carbohydrate, nucleic acid, lipid, polysaccharide or combinations thereof, or synthetic inorganic or organic molecule, that causes a desired biological effect when administered in vivo to an animal, including but not limited to birds and mammals, including humans. Peptides can include any compound containing two or more amino-acid residues joined by amide bonds formed from the carboxyl group of one amino acid and the amino group of the next one. In some embodiments, the active agent can be a bioactive agent. Active agents can have many different types of elution profiles.

Active agents useful according to the invention include substances that possess desirable therapeutic characteristics for application to the implantation site. Active agents useful in the present invention can include many types of therapeutics including thrombin inhibitors, antithrombogenic agents, thrombolytic agents, fibrinolytic agents, anticoagulants, anti-platelet agents, vasospasm inhibitors, calcium channel blockers, steroids, vasodilators, anti-hypertensive agents, antimicrobial agents, antibiotics, antibacterial agents, antiparasite and/or antiprotozoal solutes, antiseptics, antifungals, angiogenic agents, anti-angiogenic agents, inhibitors of surface glycoprotein receptors, antimitotics, microtubule inhibitors, antisecretory agents, actin inhibitors, remodeling inhibitors, antisense nucleotides, anti-metabolites, miotic agents, anti-proliferatives, anticancer chemotherapeutic agents, anti-neoplastic agents, antipolymerases, antivirals, anti-AIDS substances, anti-inflammatory steroids or non-steroidal anti-inflammatory agents, analgesics, antipyretics, immunosuppressive agents, immunomodulators, growth hormone antagonists, growth factors, radiotherapeutic agents, peptides, proteins, enzymes, extracellular matrix components, ACE inhibitors, free radical scavengers, chelators, antioxidants, photodynamic therapy agents, gene therapy agents, anesthetics, immunotoxins, neurotoxins, opioids, dopamine agonists, hypnotics, antihistamines, tranquilizers, anticonvulsants, muscle relaxants and anti-Parkinson substances, antispasmodics and muscle contractants, anticholinergics, ophthalmic agents, antiglaucoma solutes, prostaglandins, antidepressants, antipsychotic substances, neurotransmitters, anti-emetics, imaging agents, specific targeting agents, and cell response modifiers.

More specifically, in embodiments the active agent can include heparin, covalent heparin, synthetic heparin salts, or another thrombin inhibitor; hirudin, hirulog, argatroban, D-phenylalanyl-L-poly-L-arginyl chloromethyl ketone, or another antithrombogenic agent; urokinase, streptokinase, a tissue plasminogen activator, or another thrombolytic agent; a fibrinolytic agent; a vasospasm inhibitor; a calcium channel blocker, a nitrate, nitric oxide, a nitric oxide promoter, nitric oxide donors, dipyridamole, or another vasodilator; HYTRIN® or other antihypertensive agents; a glycoprotein IIb/IIIa inhibitor (abciximab) or another inhibitor of surface glycoprotein receptors; aspirin, ticlopidine, clopidogrel or another antiplatelet agent; colchicine or another antimitotic, or another microtubule inhibitor; dimethyl sulfoxide (DMSO), a retinoid, or another antisecretory agent; cytochalasin or another actin inhibitor; cell cycle inhibitors; remodeling inhibitors; deoxyribonucleic acid, an antisense nucleotide, or another agent for molecular genetic intervention; methotrexate, or another antimetabolite or antiproliferative agent; tamoxifen citrate, TAXOL®, paclitaxel, or the derivatives thereof, rapamycin (or other rapalogs, e.g. zotarolimus or sirolimus), vinblastine, vincristine, vinorelbine, etoposide, tenopiside, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, chlorambucil, ethylenimines, methylmelamines, alkyl sulfonates (e.g., busulfan), nitrosoureas (carmustine, etc.), streptozocin, methotrexate (used with many indications), fluorouracil, floxuridine, cytarabine, mercaptopurine, thioguanine, pentostatin, 2-chlorodeoxyadenosine, cisplatin, carboplatin, procarbazine, hydroxyurea, morpholino phosphorodiamidate oligomer or other anti-cancer chemotherapeutic agents; cyclosporin, tacrolimus (FK-506), pimecrolimus, azathioprine, mycophenolate mofetil, mTOR inhibitors, or another immunosuppressive agent; cortisol, cortisone, dexamethasone, dexamethasone sodium phosphate, dexamethasone acetate, dexamethasone derivatives, betamethasone, fludrocortisone, prednisone, prednisolone, 6U-methylprednisolone, triamcinolone (e.g., triamcinolone acetonide), or another steroidal agent; trapidil (a PDGF antagonist), angiopeptin (a growth hormone antagonist), angiogenin, a growth factor (such as vascular endothelial growth factor (VEGF)), or an anti-growth factor antibody (e.g., ranibizumab, which is sold under the tradename LUCENTIS®, or bevacizumab, which is sold under the tradename AVASTIN®), or another growth factor antagonist or agonist; dopamine, bromocriptine mesylate, pergolide mesylate, or another dopamine agonist; $^{60}$Co (5.3 year half life), $^{192}$Ir (73.8 days), $^{32}$P (14.3 days), $^{111}$In (68 hours), $^{90}$Y (64 hours), $^{99}$Tc (6 hours), or another radiotherapeutic agent; iodine-containing compounds, barium-containing compounds, gold, tantalum, platinum, tungsten or another heavy metal functioning as a radiopaque agent; a peptide, a protein, an extracellular matrix component, a cellular component or another biologic agent; captopril, enalapril or another angiotensin converting enzyme (ACE) inhibitor; angiotensin receptor blockers; enzyme inhibitors (including growth factor signal transduction kinase inhibitors); ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, 131I-, 32P- or $^{36}$S-radiolabelled form or other radiolabelled form of any of the foregoing; an estrogen (such as estradiol, estriol, estrone, and the like) or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluorozinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin, or other antibody targeted therapy agents; gene therapy agents; enalapril and other prodrugs; PROSCAR®, HYTRIN® or other agents for treating benign prostatic hyperplasia (BHP); mitotane, aminoglutethimide, breveldin, acetaminophen, etodalac, tolmetin, ketorolac, ibuprofen and derivatives, mefenamic acid, meclofenamic acid, piroxicam, tenoxicam, phenylbutazone, oxyphenbutazone, nabumetone, auranofin, aurothioglucose, gold sodium thiomalate, a mixture of any of these, or derivatives of any of these.

Other biologically useful compounds that can also be included in the coating include, but are not limited to, hormones, β-blockers, anti-anginal agents, cardiac inotropic agents, corticosteroids, analgesics, anti-inflammatory agents, anti-arrhythmic agents, immunosuppressants, anti-bacterial agents, anti-hypertensive agents, anti-malarials, anti-neoplastic agents, anti-protozoal agents, anti-thyroid agents, sedatives, hypnotics and neuroleptics, diuretics, anti-parkinsonian agents, gastro-intestinal agents, anti-viral agents, anti-diabetics, anti-epileptics, anti-fungal agents, histamine H-receptor antagonists, lipid regulating agents, muscle relaxants, nutritional agents such as vitamins and minerals, stimulants, nucleic acids, polypeptides, and vaccines.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, geldanamycin analogs, cephalosporins, or the like. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of anti-viral agents include α-methyl-1-adamantanemethylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(−), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacin, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances that have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

Cell response modifiers are chemotactic factors such as platelet-derived growth factor (PDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor alpha, fibroblast growth factor, platelet-derived endothelial cell growth factor, insulin-like growth factor, nerve growth factor, bone growth/cartilage-inducing factor (alpha and beta), and matrix metalloproteinase inhibitors. Other cell response modifiers are the interleukins, interleukin receptors, interleukin inhibitors, interferons, including alpha, beta, and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins, antisense molecules, androgenic receptor blockers and statin agents.

In an embodiment, the active agent used with the invention includes compounds having a steroid ring system. Compounds having a steroid ring system can be referred to as steroids. In an embodiment, the active agent is a steroid. Steroids include both naturally occurring compounds and synthetic analogues based on the cyclopenta[a]phenanthrene carbon skeleton, partially or completely hydrogenated. Steroids can include glucocorticoids, estrogens and androgens. By way of example, steroids can include dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fludrocortisone, fludrocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel, analogs thereof, or combinations thereof.

Active agents used with the invention can include macromolecules, small molecules, hydrophilic molecules, hydrophobic molecules, and the like. Macromolecular active agents used with embodiments of the invention can include proteins, nucleic acids, and polysaccharides. By way of example, proteins can include glycosylated proteins, antibodies (both monoclonal and polyclonal), antibody derivatives (including diabodies, f(ab) fragments, humanized antibodies, etc.), cytokines, growth factors, receptor ligands, enzymes, and the like. Nucleic acids can include RNA, DNA, cDNA, siRNA, and the like.

In an embodiment, macromolecular active agents used with the invention have a molecular weight (or average molecular weight) of greater than about 10 kD (1 kilodalton is equal to 1,000 atomic mass units). In an embodiment, the macromolecular active agent includes a peptide of greater than about 10 kD. In an embodiment, the macromolecular active agent includes a peptide of greater than about 100 kD.

In some embodiments, the active agent of the coating can include agents that are small molecules. In some embodiments, the active agent can include therapeutic agents that are hydrophilic small molecules. In some embodiments, the active agent can include therapeutic agents that are hydrophobic small molecules. As used herein, small molecules can include those with a molecular weight of equal to or less than 10 kilodaltons. In an embodiment, small molecules have a molecular weight of less than about 5 kilodaltons. Small molecules can include many types of therapeutics including those as described above with respect to macromolecules (e.g., thrombin inhibitors, antithrombogenic agents, etc.).

In some embodiments, more than one active agent can be used as a part of the coating material. Specifically, co-agents or co-drugs can be used. A co-agent or co-drug can act differently than the first agent or drug. The co-agent or co-drug can have an elution profile that is different than the first agent or drug. In some embodiments, accessory molecules are included such as chaperonins.

Devices

Embodiments of the invention can be used to coat many different types of devices including medical devices. Medical devices can include both implantable devices and non-implantable medical devices.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, embodiments of the invention can be utilized in connection with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, embodiments of the invention can be utilized in connection with ophthalmic devices configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. No. 6,719,750 B2 ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), 2003/0014036 A1 ("Reservoir Device for Intraocular Drug Delivery," Varner et al.), 2005/0276837 ("Controlled Release Bioactive Agent Delivery Device", Anderson et al.), 2005/0271706 ("Controlled Release Bioactive Agent Delivery Device", Anderson et al.), 2005/0287188 ("Controlled Release Bioactive Agent Delivery Device", Anderson et al.), 2005/0271703 ("Controlled Release Bioactive Agent Delivery Device", Anderson et al.), 2005/0281863 ("Controlled Release Bioactive Agent Delivery Device", Anderson et al.), and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. application Ser. No. 11/175, 850 ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

Methods of Applying Combination Degradable/Non-Degradable Coating

It will be appreciated that many different techniques may be used to apply combination degradable/non-degradable coatings to a substrate. By way of example, techniques can include spray deposition, vapor deposition, dip coating, brush coating, printing, and the like. In some embodiments, the combination degradable/non-degradable coating is sprayed onto a substrate.

In some embodiments, the degradable polymer and the non-degradable polymer used have compatible solvent requirements. In other embodiments, the degradable polymer and the non-degradable polymer used have incompatible solvent requirements.

By way of example, in some cases, the degradable polymer used may be primarily soluble in aqueous solvents while the non-degradable polymer used may be primarily soluble in non-polar organic solvents. In other cases, the degradable polymer used may be primarily soluble in non-polar organic solvents while the non-degradable polymer used may be primarily soluble in aqueous solvents. In still other cases the degradable polymer and the non-degradable polymer may be soluble in a non-polar organic solvent while the active agent is not.

In some cases it may be difficult to combine the degradable polymer, the non-degradable polymer, and the active agent while maintaining relatively uniform dispersal of one within the others because the particular solvents used and/or the components themselves favor phase separation. However, in some embodiments, keeping components separate until application onto a substrate, where the solvent quickly flashes off, can facilitate the application of such components having incompatible solvent requirements. For example, in an embodiment, the invention includes a method of applying a combination degradable/non-degradable coating including spraying a degradable polymer solution from a first spray head or nozzle while simultaneously spraying a non-degradable polymer solution from a second spray head or nozzle. Spraying solutions from multiple spray heads or nozzles can offer the advantage of keeping components with incompatible solvent requirements separate until application onto the substrate. Thus, it is believed that spraying solutions from multiple spray heads or nozzles can offer the advantage generating a more uniform dispersal of the degradable polymer within the non-degradable polymer and vice versa.

The active agent can be included with either the degradable or the non-degradable polymer solution or it may be provided as a solution separate from the degradable and non-degradable polymer solutions. By way of example, where the active agent is a macromolecule such as a protein it may be included with the degradable polymer solution. While not intending to be bound by theory, it is believed that this can help preserve the activity of the active agent. In an embodiment, the active agent is sprayed from a third spray head or nozzle. In an embodiment, the active agent is combined with the degradable solution.

U.S. Publ. Pat. Application No. 2007/0128343, entitled "Apparatus and Methods for Applying Coatings", the contents of which is herein incorporated by reference, describes various techniques of applying a coating from multiple spray heads and related equipment. The spray heads or nozzles can be of a gas-atomization type or of an ultrasonic atomization type. In some embodiments, the spray heads or nozzles are ultrasonic.

The degradable polymer solution, the non-degradable polymer solution, and/or the active agent solution can be delivered from a supply reservoir to a spray head or nozzle at a desired rate. By way of example, the solutions can be delivered at a rate of about 0.01 mL to about 1 mL per minute. Application of the solution to the spray head at a rate too high can result in solvent build-up on the substrate which may adversely affect the inter-dispersion of the degradable polymer and the non-degradable polymer. Application of the solution to the spray head at a rate too high can also result in an uneven sputtering of the solution instead of a uniform and controlled spray stream. In an embodiment, the solutions are delivered at a rate of less than 1 mL/min. In an embodiment, the solutions are delivered at a rate of about 0.01 mL/min to about 0.2 mL/min.

In some instances, the degradable polymer solution, the non-degradable polymer solution, and/or the active agent solution can include incompatible components that are formed into an emulsion for application via the spray head or nozzle.

In some embodiments, a top coat is applied over a combination degradable/non-degradable coating layer. The top coat can further serve to control elution of an active agent. The top coat can include degradable polymers, non-degradable polymers, or both. In an embodiment, the top coat includes parylene. In an embodiment, the top coat includes pBMA and/or pEVA. In an embodiment, the top coat includes an active agent.

The present invention may be better understood with reference to the following examples. These examples are intended to be representative of specific embodiments of the invention, and are not intended as limiting the scope of the invention.

EXAMPLES

Example 1

Application of Degradable/Non-Degradable Matrix

Poly-n-butylmethacrylate (pBMA) and polyethylene-co-vinyl acetate (pEVA) were combined with chloroform to form a non-degradable polymer solution having 25 mg/mL pBMA and 25 mg/mL pEVA (total solids concentration of 50 mg/mL). NaPS (sodium persulfate) was combined with distilled deionized water to form a solution having a concentration of 44 mg/mL NaPS. 10 mL of the non-degradable polymer solution was combined with 0.5 mL of the NaPS solution (44 mg/mL) and the resulting solution was turned into a emulsion by a high speed mixer (TISSUE-TEAROR, Biospec Products Model 398, operated at 15,000 rpm for 30 seconds).

A stock solution of TEMED (N,N,N',N'-tetramethylethylenediamine) was formed by mixing 1 mL TEMED with 2 mL 4M HCl. 6.5 mL of a solution containing 100 mg/mL of OCTODEX DS-16 (polydextran hydroxyethylmethacrylate) ("DS-16") in water was mixed with 0.9 mL of the TEMED stock solution and 3.5 mL of a solution containing 100 mg/mL BSA in water to form a degradable polymer solution.

Stainless steel stents were obtained from Orbus Neich, Fort Lauderdale, Fla. A layer of parylene was deposited over each stent using a standard vapor deposition process.

The emulsion was applied onto the exterior surface of a first ultrasonic nozzle (60 KHz ultrasonic nozzle from Sono-Tek, Milton, N.Y.) operating at about 1.0 watt, generating an atomized spray stream of the emulsion directed at the substrate to be coated. Simultaneously, the degradable polymer solution was applied onto the exterior surface of a second ultrasonic nozzle (60 KHz ultrasonic nozzle from Sono-Tek, Milton, N.Y.) operating at about 1.0 watt, generating an atomized spray stream of the degradable polymer solution directed at the substrate to be coated.

For a first set of stents, the emulsion was applied through a supply tube onto the first ultrasonic nozzle at a rate of 0.09 ml/minute and the degradable component solution was applied through a supply tube onto the second ultrasonic nozzle at a rate of 0.03 ml/minute. This treatment resulted in a coating having approximately 14.0% BSA, 26.0 wt. % DS-16, 30.0 wt. % pBMA, and 30.0 wt. % pEVA. A top coat was then applied by continuing to deliver the emulsion through a supply tube at a rate of 0.09 ml/minute and stopping the flow of the degradable component solution. For this set of stents, the total average protein loading was calculated to be about 351 µg.

For a second set of stents, the emulsion was applied through a supply tube at a rate of 0.09 ml/minute and the degradable component solution was applied through a supply tube at a rate of 0.03 ml/minute. This treatment resulted in a coating having approximately 14.0% BSA, 26.0 wt. % DS-16, 30.0 wt. % pBMA, and 30.0 wt. % pEVA. For this set of stents, the total average protein loading was calculated to be about 397 µg. No top coat was applied to the second set of stents.

The elution rate of the BSA from the coated stents was then tested. Coated stents were placed in microcentrifuge tubes in 200 µL of a solution of 1×PBS. At predetermined intervals for 63 days, the entire volume of the eluent solution was replaced and then tested using the Bradford method assay (dye obtained from Sigma Chemical Co., St. Louis, Mo.). The average percentage elution of BSA is shown below in Table 1. The results are also shown in FIG. 1. The results show that a combination degradable/non-degradable matrix can be used to control elution of a component such as BSA.

TABLE 1

| Day | Set 1 (topcoat) | Set 2 (no topcoat) |
|---|---|---|
| 0 | 0% | 0% |
| 1 | 7.66% | 18.11% |
| 2 | 8.32% | 26.04% |
| 5 | 11.50% | 28.45% |
| 12 | 15.05% | 31.00% |
| 19 | 16.96% | 32.24% |
| 26 | 19.57% | 33.41% |
| 34 | 20.25% | 33.99% |

Raman spectroscopy was used to generate a cross-sectional image of the relative distribution of the components within the layer. Analysis of the cross-sectional images revealed that the BSA was co-located with the OCTODEX DS-16 and that the OCTODEX DS-16 and the pEVA/pBMA components were relatively well dispersed within each other. This example shows that a degradable polymer and a non-degradable polymer having incompatible solvent requirements can be evenly dispersed in one another in some embodiments of the invention.

Example 2

Application of Degradable/Non-Degradable Matrix

Poly-n-butylmethacrylate (pBMA) and polyethylene-co-vinyl acetate (pEVA) were combined with chloroform to form a non-degradable polymer solution having 12.5 mg/mL pBMA and 12.5 mg/mL pEVA (total solids concentration of 25 mg/mL). NaPS (sodium persulfate) was combined with distilled deionized water to form a solution having a concentration of 44 mg/mL NaPS. 10 mL of the non-degradable polymer solution was combined with 0.5 mL of the NaPS solution (44 mg/mL) and the resulting solution was turned into a emulsion by a high speed mixer (TISSUE-TEAROR, Biospec Products Model 398, operated at 15,000 rpm for 30 seconds).

A stock solution of TEMED (N,N,N',N'-tetramethylethylenediamine) was formed by mixing 1 mL TEMED with 2 mL 4M HCl. 5 mL of a solution containing 150 mg/mL of OCTODEX DS-16 (polydextran hydroxyethylmethacrylate) in water was mixed with 0.9 mL of the TEMED stock solution and 5 mL of a solution containing 50 mg/mL IgG antibodies in water (in a 1:5 ratio of IgG rabbit anti-goat antibodies to IgG rabbit nonspecific antibodies, antibodies obtained from Lampire Biological Laboratories, Pipersville, Pa.) to form a degradable polymer solution.

Stainless steel stents were obtained from Orbus Neich, Fort Lauderdale, Fla. A layer of parylene was deposited over each stent using a standard vapor deposition process.

The emulsion was applied onto the exterior surface of a first ultrasonic nozzle (60 KHz ultrasonic nozzle from Sono-Tek, Milton, N.Y.) operating at about 1.0 watt, generating an atomized spray stream of the emulsion directed at the substrate to be coated. Simultaneously, the degradable polymer solution was applied onto the exterior surface of a second ultrasonic nozzle (60 KHz ultrasonic nozzle from Sono-Tek, Milton, N.Y.) operating at about 1.0 watt, generating an atomized spray stream of the degradable polymer solution directed at the substrate to be coated.

For a first set of stents (5), the emulsion was applied through a supply tube onto the first ultrasonic nozzle at a rate of 0.09 ml/minute and the degradable component solution was applied through a supply tube onto the second ultrasonic nozzle at a rate of 0.03 ml/minute. This treatment resulted in a coating having approximately 14.06 wt. % IgG, 42.17 wt. % DS-16, 21.9 wt. % pBMA, and 21.9 wt. % pEVA. A top coat was then applied by continuing to deliver the emulsion through a supply tube at a rate of 0.09 ml/minute and stopping the flow of the degradable component solution. For this set of stents, the total average protein loading was calculated to be about 268.55 µg.

For a second set of stents (5), the emulsion was applied through a supply tube at a rate of 0.09 ml/minute and the degradable component solution was applied through a supply tube at a rate of 0.03 ml/minute. This treatment resulted in a coating having approximately 14.06% wt. IgG, 42.17 wt. % DS-16, 21.9 wt. % pBMA, and 21.9 wt. % pEVA. For this set of stents, the total average protein loading was calculated to be about 347.12 µg. No top coat was applied to the second set of stents.

Figure 2:
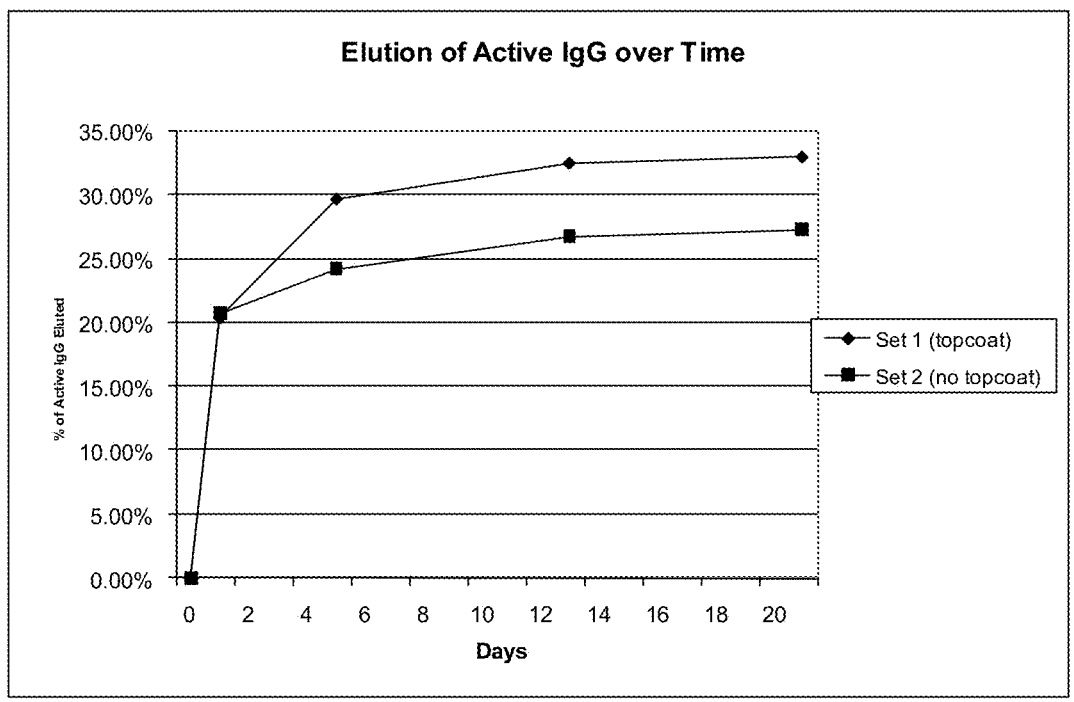
FIG. 2 is a graph showing the elution of active IgG from a coating in accordance with another embodiment of the invention.
Figure 3:
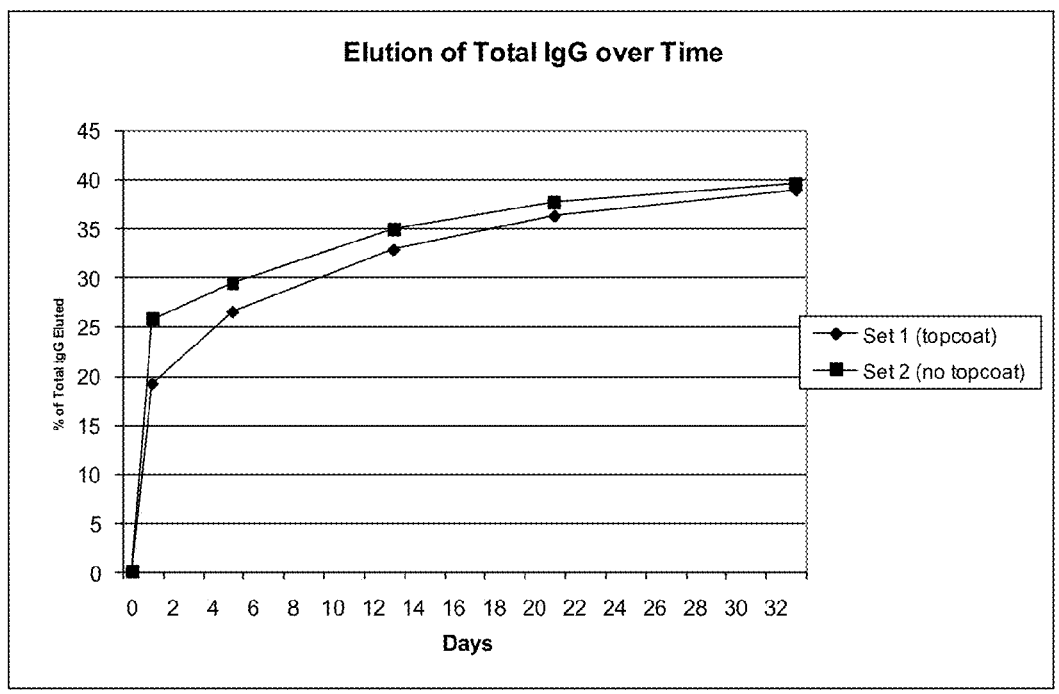
FIG. 3 is a graph showing the elution of total IgG from a coating in accordance with another embodiment of the invention.

The elution rate of the IgG antibodies from the coated stents was then tested. Coated stents were placed in microcentrifuge tubes in 500 µL, of a solution of 1×PBS. At predetermined intervals for 63 days, 200 µL, of the eluent solution was removed, divided into two 100 µL, aliquots, and placed into two 96 well plates. The remaining 300 µL, was removed from the microcentrifuge tube, and 0.5 mL of fresh eluent solution (1×PBS) was added to the microcentrifuge tube having the stent. The eluent samples in 96 well plates were analyzed for active rabbit antibody release using an Enzyme-Linked Immunosorbent Assay (ELISA). Briefly, the 100 µL, of eluent solution was incubated at 37° Celsius for one hour and then washed 3× with 2 ml PBS/Tween 20 (Sigma). The wells were blocked with 100 µL, StabilCoat (SurModics, Eden Prairie, Minn.) for 1 hour at room temperature and then washed 3× with 2 ml PBS/Tween 20. 100 µL, of either 0.1 µg/mL (in PBS/Tween) HRP (Sigma; catalog #P8375) for molecule activity or 0.08 µg/mL (in PBS/Tween) HRP-labeled Goat anti-Rabbit IgG (Jackson Immunological; catalog #11-305-003) was added to each well and incubated for 1 hour at 37° Celsius. The wells were washed 6 times with 2 ml PBS/Tween 20. 100 µL of TMB Microwell Peroxidase Substrate System (KPL, Catalog #50-76-00; Gaithersburg, Md.) was added to each well. After 15 minutes, the 96 well plate was analyzed for HRP conjugate on a spectrophotometer (Tecan) at 650 nm absorbance. Detectable antibody was found in the eluate samples at each time point. The eluent samples were also analyzed for total IgG release (specific and non-specific) using the Bradford method assay (dye obtained from Sigma Chemical Co., St. Louis, Mo.). The percentage elution of active IgG is shown below in Table 3 as a percentage of total active IgG. The results are also shown in FIG. 2. The percentage elution of total IgG is shown below in Table 4 (and also in FIG. 3). The results show that a combination degradable/non-degradable matrix can be used to control elution of an active agent. The results also show that a combination degradable/non-degradable matrix can be used to elute an active agent while retaining the activity of the active agent.

TABLE 3

| | % Elution of Active IgG | |
|---|---|---|
| Day | Set 1 (topcoat) | Set 2 (no topcoat) |
| 0 | 0.00% | 0.00% |
| 1 | 20.39% | 20.72% |
| 5 | 29.71% | 24.18% |

TABLE 3-continued

% Elution of Active IgG

| Day | Set 1 (topcoat) | Set 2 (no topcoat) |
| --- | --- | --- |
| 13 | 32.51% | 26.79% |
| 21 | 33.00% | 27.32% |

TABLE 4

Elution of Total IgG

| Day | Set 1 (topcoat) | Set 2 (no topcoat) |
| --- | --- | --- |
| 0 | 0% | 0% |
| 1 | 19.13% | 25.74% |
| 5 | 26.44% | 29.40% |
| 13 | 32.76% | 34.91% |
| 21 | 36.20% | 37.61% |
| 33 | 38.83% | 39.54% |

Example 3

Application of Degradable/Non-Degradable Matrix

Poly-n-butylmethacrylate (pBMA) and polyethylene-co-vinyl acetate (pEVA) were combined in equal parts with a solvent of chloroform to form a non-degradable polymer solution having 10 mg/ml pBMA and 10 mg/ml pEVA (total solids concentration of 20 mg/ml).

IgG antibodies (in a ratio of 1:10 IgG rabbit anti-goat antibodies to IgG rabbit non-specific antibodies, antibodies obtained from Lampire Biological Laboratories, Pipersville, Pa.) were combined with OCTODEX DS-12 (polydextran hydroxyethylmethacrylate) and DBDS (4,5-bis-(4-benzoylphenylmethyleneoxy)benzene-1,3-disulfonic acid disodium salt) in PBS to form a degradable coating solution having 12.5 mg/mL IgG, 50 mg/mL DS-12, and 0.5 mg/mL DBDS.

MP-35N alloy coils were used as a substrate. The non-degradable polymer solution was applied onto the exterior surface of a first ultrasonic nozzle (60 KHz ultrasonic nozzle from Sono-Tek, Milton, N.Y.) operating at about 1.0 watt. Simultaneously, the degradable coating solution was applied onto the exterior surface of a second ultrasonic nozzle (60 KHz ultrasonic nozzle from Sono-Tek, Milton, N.Y.) operating at about 1.0 watt. A UV light source (the UV light was a DYMAX BLUE-WAVE 200 operating at 330 nm between about 1 and 2 mW/cm$^2$) was used to shine light on the substrate as the coating was being applied. The UV light interacted with the DBDS to generate a free radical and cross-link the OCTODEX DS-12.

For a first set of coils, the non-degradable polymer solution was applied through a supply tube at a rate of 0.07 mL/minute and the degradable component solution was applied through a supply tube at a rate of 0.02 mL/minute. This treatment resulted in a coating having approximately 9.40% IgG, 37.59 wt. % DS-12, 26.31 wt. % pBMA, and 26.31 wt. % pEVA. The total active protein loading was calculated to be about 152.12 µg on average. A top coat was then applied by continuing to deliver the non-degradable polymer solution through a supply tube at a rate of 0.07 mL/minute and stopping the flow of the degradable component solution.

For a second set of coils, the non-degradable component solution was applied through a supply tube at a rate of 0.07 mL/minute and the degradable component solution was applied through a supply tube at a rate of 0.02 mL/minute. This treatment resulted in a coating having approximately 9.40 wt. % IgG, 37.59 wt. % DS-12, 26.31 wt. % pBMA, and 26.31 wt. % pEVA. The total active protein loading was calculated to be about 146.51 µg on average. No top coat was applied to the second set of coils.

Figure 4:
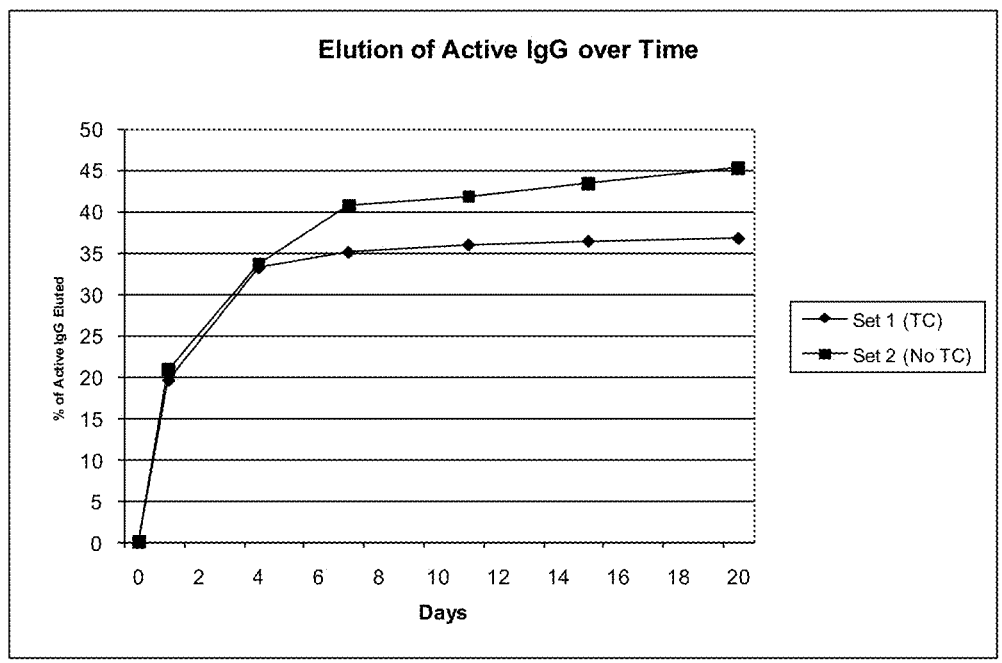
FIG. 4 is a graph showing the elution of active IgG from a coating in accordance with another embodiment of the invention.
Figure 5:
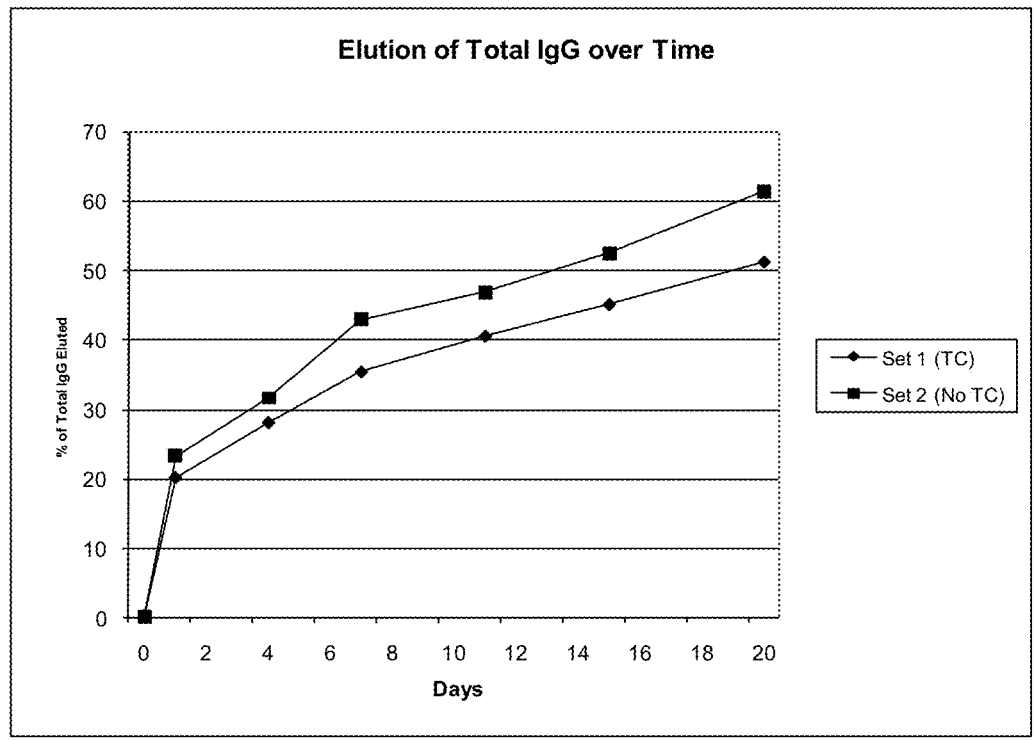
FIG. 5 is a graph showing the elution of total IgG from a coating in accordance with another embodiment of the invention.

The % elution of active IgG antibodies from the coated stents was then tested as described in Example 1 above. The % elution of total IgG antibodies (both specific and non-specific antibodies) was assessed using QUANT-IT protein assay kit available from Invitrogen, Carlsbad, Calif. The results are shown in Tables 5-6 below and in FIGS. 4-5.

TABLE 5

(% Elution of Active IgG)

| Day | Set 1 (TC) | Set 2 (No TC) |
| --- | --- | --- |
| 0 | 0% | 0% |
| 1 | 19.57% | 20.82% |
| 4 | 33.20% | 33.67% |
| 7 | 35.08% | 40.59% |
| 11 | 35.98% | 41.79% |
| 15 | 36.45% | 43.35% |
| 20 | 36.77% | 45.26% |

TABLE 6

(% Elution of Total IgG)

| Day | Set 1 (TC) | Set 2 (No TC) |
| --- | --- | --- |
| 0 | 0 | 0 |
| 1 | 20.11 | 23.30 |
| 4 | 28.07 | 31.64 |
| 7 | 35.37 | 42.94 |
| 11 | 40.51 | 46.87 |
| 15 | 45.07 | 52.50 |
| 20 | 51.22 | 61.46 |

Example 4

Application of Degradable/Non-Degradable Matrix

Poly-n-butylmethacrylate (pBMA) and polyethylene-co-vinyl acetate (pEVA) were combined with chloroform to form a non-degradable polymer solution having 20 mg/ml pBMA and 20 mg/ml pEVA (total solids concentration of 40 mg/ml).

Poly(butyleneterephthalate-co-ethylene glycol) "1000PEG80" (80 wt. % polyethylene glycol (PEG) and 20 wt. % butyleneterephthalate (PBT), the PEG having an average molecular weight of 1000 kD) in chloroform was combined with BSA in varying concentrations in phosphate buffered saline to form a first degradable solution having 45 mg/ml 1000PEG80 and 5 mg/ml BSA and a second degradable solution having 40 mg/ml 1000PEG80 and 10 mg/ml BSA. The first and second degradable solutions were turned into an emulsion by using a mixer (TISSUE-TEAROR, Biospec Products, Inc. Model 398, 10,000 rpm for 30 seconds).

Stainless steel stents were obtained from Orbus Neich, Fort Lauderdale, Fla. A layer of parylene was deposited over each stent using a standard vapor deposition process.

The emulsion (first or second degradable solution) was applied onto the exterior surface of a first ultrasonic nozzle (60 KHz ultrasonic nozzle from Sono-Tek, Milton, N.Y.) operating at about 1.0 watt. Simultaneously, the non-degradable polymer solution was applied onto the exterior surface of a second ultrasonic nozzle (60 KHz ultrasonic nozzle from Sono-Tek, Milton, N.Y.) operating at about 1.0 watts.

For a first set of stents, the first degradable solution was applied through a supply tube at a rate of 0.05 ml/minute and the non-degradable component solution was applied through a supply tube at a rate of 0.05 ml/minute. This treatment resulted in a coating having approximately 5.88 wt. % BSA, 50.0 wt. % 1000PEG80, 22.22 wt. % pBMA, and 22.22 wt. % pEVA. The total protein loading was calculated to be about 73 μg on average.

For a second set of stents, the second degradable solution was applied through a supply tube at a rate of 0.05 ml/minute and the non-degradable component solution was applied through a supply tube at a rate of 0.05 ml/minute. This treatment resulted in a coating having approximately 11.11% BSA, 44.44 wt. % 1000PEG80, 22.22 wt. % pBMA, and 22.22 wt. % pEVA. The total protein loading was calculated to be about 147 μg on average.

Figure 6:
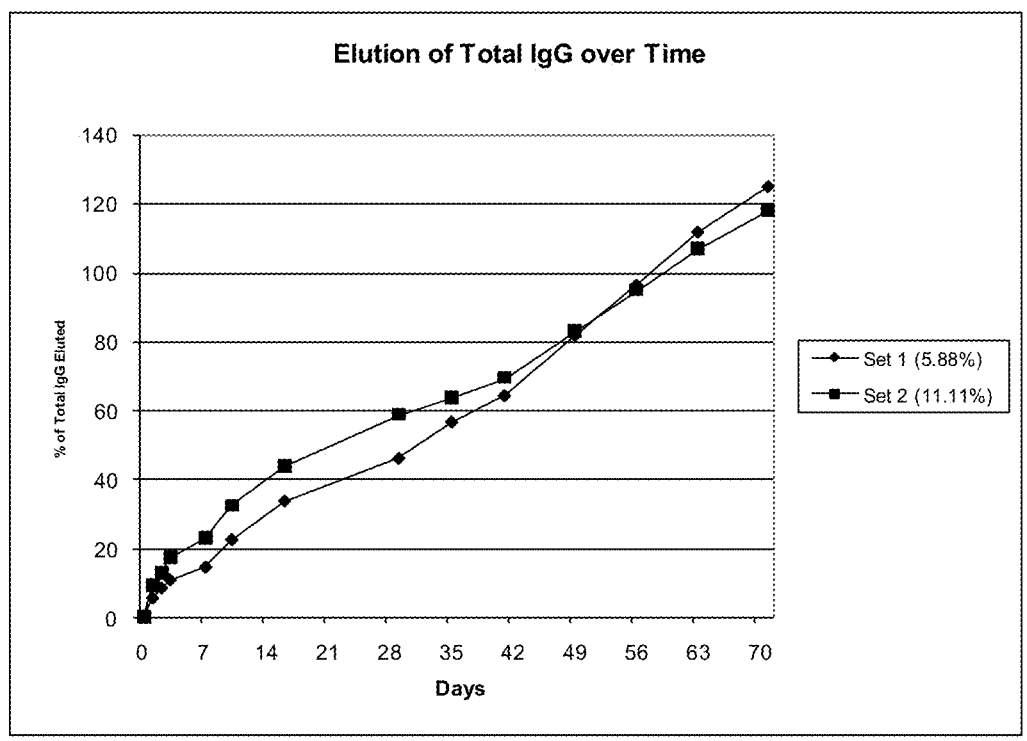
FIG. 6 is a graph showing the elution of total IgG from a coating in accordance with another embodiment of the invention.

The elution rate of the BSA from the coated stents was then tested. Specifically, the stents were put into 400 μl of PBS and kept at 37 degrees Celsius. The solution was replaced at various time points and then analyzed for protein content using the Bradford method assay (dye obtained from Sigma Chemical Co., St. Louis, Mo.). The results are shown in Table 7 below and in FIG. 6.

TABLE 7

| Day | Set 1 (5.88%) | Set 2 (11.11%) |
|---|---|---|
| 0 | 0 | 0 |
| 1 | 5.49 | 9.25 |
| 2 | 8.33 | 12.95 |
| 3 | 10.75 | 17.39 |
| 7 | 14.46 | 23.06 |
| 10 | 22.46 | 32.43 |
| 16 | 33.61 | 43.70 |
| 29 | 45.97 | 58.74 |
| 35 | 56.50 | 63.58 |
| 41 | 64.20 | 69.44 |
| 49 | 81.66 | 83.04 |
| 56 | 96.19 | 94.93 |
| 63 | 111.61 | 106.67 |
| 71 | 124.81 | 118.10 |

Example 5

Application of Degradable/Non-Degradable Matrix

Poly-n-butylacrylate (pBMA), polyethylene-co-vinyl acetate (pEVA) and poly(butyleneterephthalate-co-ethylene glycol) 1000PEG55 (55 wt. % polyethylene glycol (PEG) and 45 wt. % butyleneterephthalate (PBT), the PEG having an average molecular weight of 1000 Daltons) were combined in a solvent of chloroform to form a polymer solution having 12.5 mg/ml pBMA, 12.5 mg/ml pEVA and 25 mg/ml poly (butyleneterephthalate-co-ethylene glycol) (1000PEG55) (total solids concentration of 50 mg/ml). IgG (at a ratio of 1:9 IgG rabbit anti-goat antibodies to IgG rabbit non-specific antibodies) was combined with PBS to form a solution having 50 mg/ml IgG.

Stainless steel stents were obtained from Orbus Neich, Fort Lauderdale, Fla. A layer of parylene was deposited over each stent using a standard vapor deposition process.

The polymer solution was applied onto the exterior surface of a first ultrasonic nozzle (60 KHz ultrasonic nozzle from Sono-Tek, Milton, N.Y.) operating at about 0.5 to 1.5 watts. Simultaneously, the IgG solution was applied onto the exterior surface of a second ultrasonic nozzle (60 KHz ultrasonic nozzle from Sono-Tek, Milton, N.Y.) operating at about 0.5 to 1.5 watts.

The polymer solution was applied through a supply tube at a rate of 0.12 ml/minute and the IgG solution was applied through a supply tube at a rate of 0.03 ml/minute. This treatment resulted in a coating having approximately 20.00 wt. % pBMA, 20.00 wt. % pEVA, 40.00 wt. % 1000PEG80 and 20.00% IgG. The total active protein loading was calculated to be about 500.2 μg on average.

Figure 7:
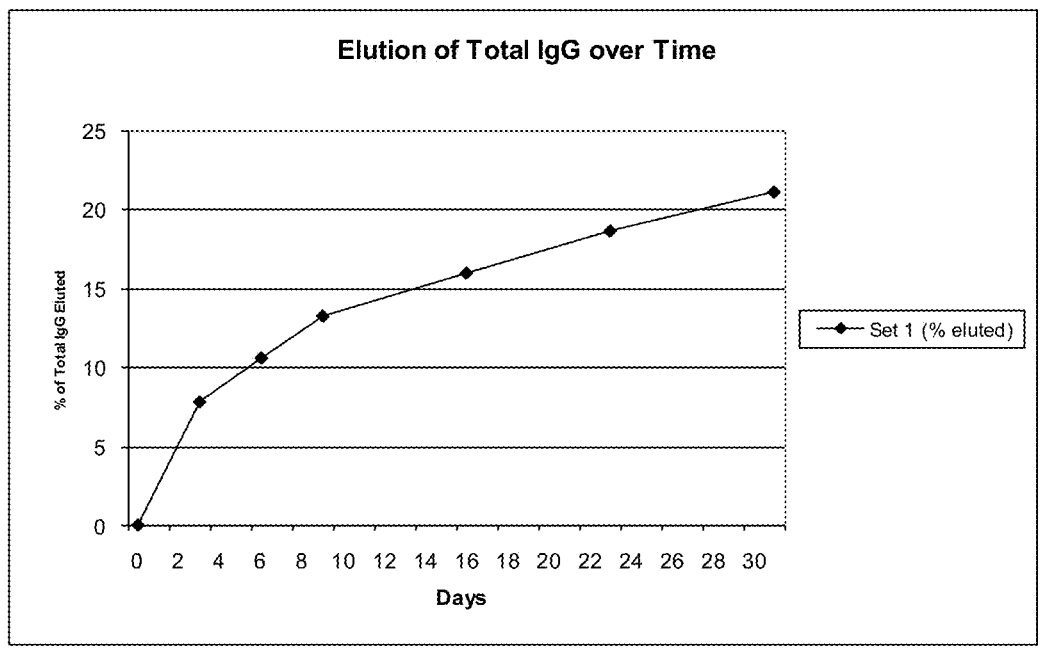
FIG. 7 is a graph showing the elution of total IgG from a coating in accordance with another embodiment of the invention.
Figure 8:
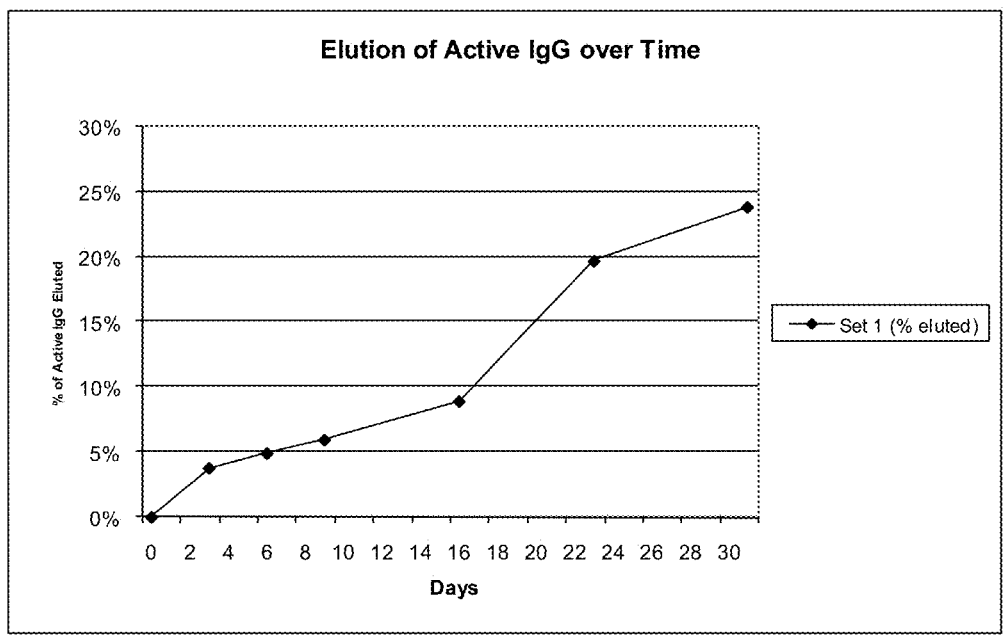
FIG. 8 is a graph showing the elution of active IgG from a coating in accordance with another embodiment of the invention.

The elution rate of the IgG from the coated stents was then tested. Specifically, the stents were put into 500 μl of PBS and kept at 37 degrees Celsius. The solution was replaced at various time points and then analyzed for IgG content. Total IgG was assessed using the Bradford method assay (dye obtained from Sigma Chemical Co., St. Louis, Mo.). Active IgG was assessed using the ELISA assay as described in example 2 above. The results are shown in Tables 8-9 below and in FIGS. 7-8.

TABLE 8

Elution of Total IgG

| Day | Set 1 (total % eluted) |
|---|---|
| 0 | 0% |
| 3 | 7.81% |
| 6 | 10.59% |
| 9 | 13.25% |
| 16 | 15.98% |
| 23 | 18.65% |
| 31 | 21.12% |

TABLE 9

Elution of Active IgG

| Day | Set 1 (total % eluted) |
|---|---|
| 0 | 0% |
| 3 | 3.77% |
| 6 | 4.91% |
| 9 | 5.93% |
| 16 | 8.91% |
| 23 | 19.68% |
| 31 | 23.84% |

Example 6

Application of Degradable/Non-Degradable Matrix

Poly-n-butylmethacrylate (pBMA) and polyethylene-co-vinyl acetate (pEVA) were combined in a solvent of chloroform to form a non-degradable polymer solution having 15 mg/ml pBMA and 15 mg/ml pEVA (total solids concentration of 30 mg/ml).

IgG rabbit anti-goat antibodies were obtained from Sigma-Aldrich, Milwaukee, Wis. These IgG rabbit anti-goat antibodies were combined with non-specific IgG rabbit antibodies in a ratio of 5:1 non-specific to specific. These antibodies were combined with a maltodextrin-acrylate macromer "MD-acrylate" (MD-acrylate was prepared as described in U.S. Publ. Patent Application No. 2007/0065481, entitled "COATINGS INCLUDING NATURAL BIODEGRADABLE POLYSACCHARIDES AND USES THEREOF", herein incorporated by reference) in phosphate buffered saline solution and DBDS (4,5-bis-(4-benzoylphenylmethyleneoxy)benzene-1,3-disulfonic acid disodium salt) to form a degradable component solution having a concentration of 25 mg/ml (MD-acrylate), 25 mg/ml IgG antibodies (total both specific and non-specific), and 0.5 mg/ml DBDS.

MP-35N alloy coils were used as a substrate. The non-degradable polymer solution was applied onto the exterior surface of a first ultrasonic nozzle (60 KHz ultrasonic nozzle from Sono-Tek, Milton, N.Y.) operating at about 0.5 to 1.5 watts. Simultaneously, the degradable component solution was applied onto the exterior surface of a second ultrasonic nozzle (60 KHz ultrasonic nozzle from Sono-Tek, Milton, N.Y.) operating at about 0.5 to 1.5 watts.

For a first set of coils (3), the non-degradable polymer solution was applied through a supply tube at a rate of 0.02 ml/minute and the degradable component solution was applied through a supply tube at a rate of 0.02 ml/minute. This treatment resulted in a coating having approximately 33 wt. % IgG, 33 wt. % maltodextrin-acrylate, 16.5 wt. % pBMA, and 16.5 wt. % pEVA. The total protein loading (specific and non-specific IgG) was calculated to be about 400 µg on average. The total active protein loading was calculated to be about 70 µg on average.

For a second set of coils (3), the non-degradable polymer solution was applied through a supply tube at a rate of 0.046 ml/minute and the degradable component solution was applied through a supply tube at a rate of 0.023 ml/minute. This treatment resulted in a coating having approximately 25 wt. % IgG and 25 wt. % maltodextrin-acrylate, 25 wt. % pBMA, and 25 wt. % pEVA. The total protein loading (specific and non-specific IgG) was calculated to be about 400 µg on average. The total active protein loading was calculated to be about 70 µg on average.

Figure 9:
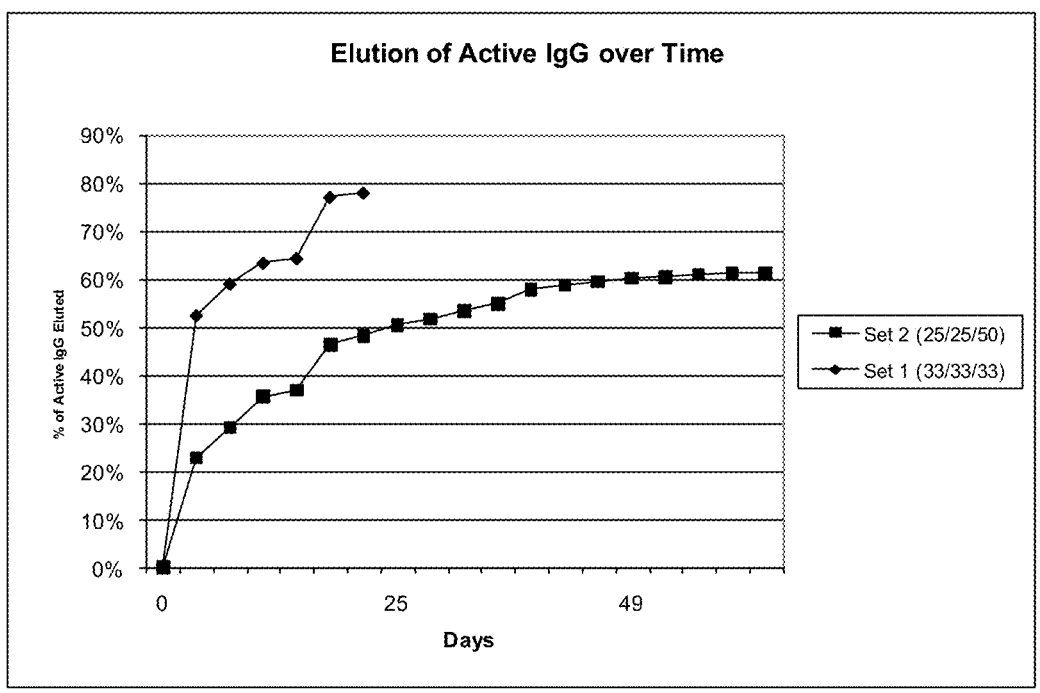
FIG. 9 is a graph showing the elution of active IgG from a coating in accordance with another embodiment of the invention.

The ultrasonic nozzles each generated an atomized stream of material that was directed at the coils. For each set of three coils, the ultrasonic nozzles were passed back and forth over one coil at a time for approximately five seconds during which the coils were rotated by a device rotator. Then the ultrasonic nozzles moved onto to spray the next coil similarly while the first coil was illuminated with UV light for approximately five seconds. The UV light was a DYMAX BLUE-WAVE 200 operating at 330 nm between about 1 and 2 mW/cm². Each spray application followed by UV illumination can be considered one cycle. Approximately 200 cycles were performed on each coil. After coating, the coils were dried in a vacuum oven at ambient temperature for 24 hours. The elution of active IgG was then tested as outlined in example 2 above (except that amylase was added at 0.12 mg/L into the solution in which the coils were bathed). The results are shown below in Table 10 and in FIG. 9.

TABLE 10

| Day | Set 1 (33/33/33) | Set 2 (25/25/50) |
|---|---|---|
| 0 | 0% | 0% |
| 3 | 52.34% | 22.83% |
| 7 | 58.85% | 29.24% |
| 10 | 63.23% | 35.59% |
| 14 | 64.14% | 36.92% |
| 17 | 76.93% | 46.39% |
| 21 | 77.79% | 48.24% |
| 25 | NA | 50.45% |
| 28 | NA | 51.82% |
| 31 | NA | 53.54% |
| 35 | NA | 54.97% |
| 38 | NA | 57.83% |
| 42 | NA | 58.91% |
| 46 | NA | 59.61% |
| 49 | NA | 60.31% |
| 52 | NA | 60.55% |
| 56 | NA | 61.06% |
| 59 | NA | 61.22% |
| 63 | NA | 61.33% |

After the elution testing procedure was performed, a cross-sectional image of the coating from one of the coils from set 2 was evaluated using scanning electron microscopy at a magnification of 2500×. The image showed that the degradable polymeric material is broken down leaving voids in the nondegradable polymeric matrix which is still structurally intact.

Example 7

Application of Degradable/Non-Degradable Matrix

Poly-n-buytlmethacrylate (pBMA), polyethylene-co-vinyl acetate (pEVA), and were combined in a solvent of chloroform to form a non-degradable polymer solution having 10 mg/ml pEVA (total solids concentration of 20 mg/ml).

IgG rabbit anti-goat antibodies were obtained from Jackson Immunological Research Laboratories, West Grove, Pa. & Sigma-Aldrich, St. Louis, Mo. The IgG rabbit anti-goat antibodies were combined with non-specific IgG rabbit antibodies at a ratio of 10:1 non-specific. These antibodies were combined with a maltodextrin-acrylate macromer "MD-acrylate" (MD-acrylate was prepared as described in U.S. Publ. Patent No. 2007/0065481, entitled "COATINGS INCLUDING NATURAL BIODEGRADABLE POLYSACCHARIDES AND USES THEREOF", herein incorporated by reference) in phosphate buffered saline solution and DBDS (4,5-bis-(4-benzoylphenylmethyleneoxy)benzene-1,3-disulfonic acid disodium salt) to form a degradable component solution having a concentration of 25 mg/ml (MD-acrylate), 25 mg/ml IgG antibodies (total both specific and non-specific), and 0.8 mg/ml DBDS.

MP-35N alloy coils were used as a substrate. The non-degradable polymer solution was applied onto the exterior surface of a first ultrasonic nozzle (60 KHz ultrasonic nozzle from Sono-Tek, Milton, N.Y.) operating at about 0.5 to 1.5 watts. Simultaneously, the degradable component solution was applied onto the exterior surface of a second ultrasonic nozzle (60 KHz ultrasonic nozzle from Sono-Tek, Milton, N.Y.) operating at about 0.5 to 1.5 watts.

For a first set of coils (34/34/16/16), the non-degradable polymer solution was applied through a supply tube at a rate of 0.03 mL/minute and the degradable component solution was applied through a supply tube at a rate of 0.025 mL/minute. This treatment resulted in a coating having approximately 34 wt. % IgG, 34 wt. % MD-acrylate, 16 wt. % pBMA, and 16 wt. % pEVA (34/34/16/16). The total protein loading (specific and non-specific IgG) was calculated to be about 600 µg on average. The total active protein loading was calculated to be about 60 µg on average.

For a second set of coils (34/34/16/16—topcoat-(25/25/25/25)), the non-degradable polymer solution was applied through a supply tube at a rate of 0.03 ml/minute and the degradable component solution was applied through a supply tube at a rate of 0.025 ml/minute. This treatment resulted in a coating having approximately 34 wt. % IgG, 34 wt. % MD-acrylate, 16 wt. % pBMA, and 16 wt. % pEVA (34/34/16/16). The total protein loading (specific and non-specific IgG) was calculated to be about 900 µg on average. The total active protein loading was calculated to be about 90 μg on average. Then, on top of this coating, a top coat was deposited by applying the non-degradable polymer solution through a supply tube at a rate of 0.05 ml/minute and the degradable top coat solution at a rate of 0.02 ml/minute. This treatment resulted in a top coat having approximately 25 wt. % IgG, and 25 wt. % MD-acrylate, 25 wt. % pBMA, and 25 wt. % pEVA (25/25/25/25).

For a third set of coils (34/34/16/16-TC(10/10/40/40)), the non-degradable polymer solution was applied through a supply tube at a rate of 0.03 ml/minute and the degradable component solution was applied through a supply tube at a rate of 0.025 ml/minute. This treatment resulted in a coating having approximately 34 wt. % IgG, 34 wt. % MD-acrylate, 16 wt. % pBMA, and 16 wt. % pEVA (34/34/16/16). The total protein loading (specific and non-specific IgG) was calculated to be about 830 μg on average. The total active protein loading was calculated to be about 83 μg on average. Then, on top of this coating, a top coat was deposited by applying the non-degradable polymer solution through a supply tube at a rate of 0.1 ml/minute and the degradable top coat solution at a rate of 0.01 ml/minute. This treatment resulted in a top coat having approximately 10 wt. % IgG, 10 wt. % MD-acrylate, 40 wt. % pBMA, and 40 wt. % pEVA (10/10/40/40).

The ultrasonic nozzles each generated an atomized stream of material that was directed at the coils. The coating was performed as described in example 6 above with cycles including five seconds of spraying and five second of UV illumination. After coating, the coils were dried in a vacuum oven at ambient temperature for 24 hours.

Figure 10:
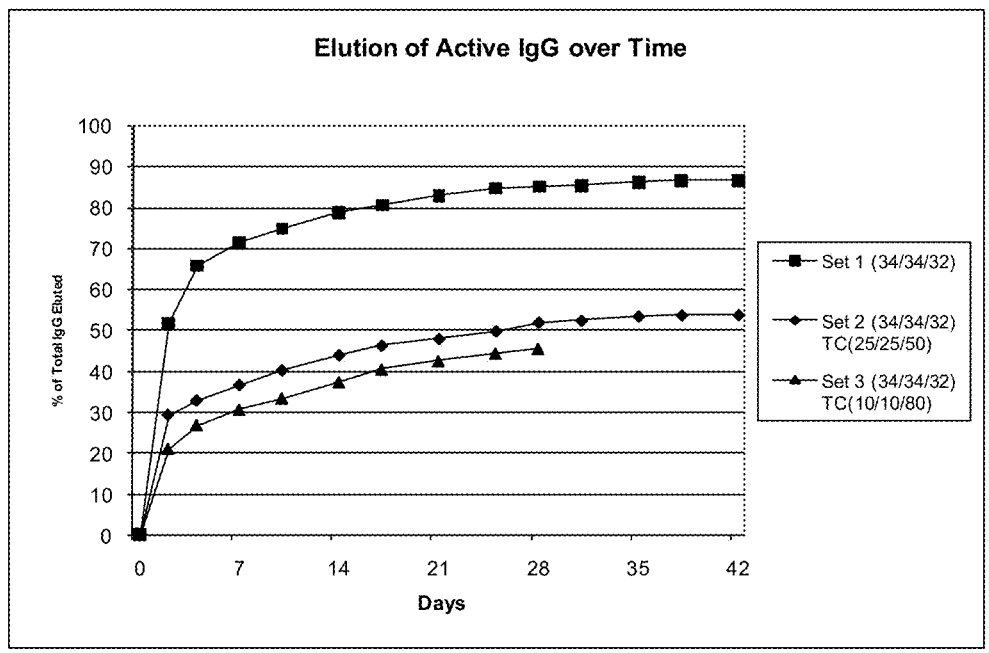
FIG. 10 is a graph showing the elution of active IgG from a coating in accordance with another embodiment of the invention.

The elution rate of the IgG antibodies from the coated coils was then tested as described in Example 2 above (except that amylase was added at 0.12 mg/L into the solution in which the coils were bathed). The results are shown in Table 11 below and in FIG. 10.

TABLE 11

| Day | Set 1 (34/34/16/16) | Set 2 (34/34/16/16) Topcoat(25/25/25/25) | Set 3 (34/34/16/16) Topcoat(10/10/40/40) |
| --- | --- | --- | --- |
| 0 | 0% | 0% | 0% |
| 2 | 51.51% | 29.21% | 21.04% |
| 4 | 65.68% | 32.72% | 26.83% |
| 7 | 71.18% | 36.45% | 30.59% |
| 10 | 74.7% | 40.05% | 33.34% |
| 14 | 78.58% | 43.78% | 37.31% |
| 17 | 80.39% | 46.03% | 40.40% |
| 21 | 82.67% | 47.66% | 42.45% |
| 25 | 84.47% | 49.58% | 44.32% |
| 28 | 85.01% | 51.68% | 45.47% |
| 31 | 85.22% | 52.14% | NA |
| 35 | 85.99% | 53.21% | NA |
| 38 | 86.39% | 53.43% | NA |
| 42 | 86.45% | 53.54% | NA |

Example 8

Release of Fab Fragments from Degradable/Non-Degradable Matrix on Coil Substrate A base coat solution was prepared by combining poly-n-butylmethacrylate (pBMA) and polyethylene-co-vinyl acetate (pEVA) in equal parts in a solvent of chloroform. The resulting base coat solution has a solids concentration of approximately 20 mg/ml.

Poly-n-butylmethacrylate (pBMA), polyethylene-co-vinyl acetate (pEVA), and poly(butyleneterephthalate-co-ethylene glycol) (1000PEG55) (55 wt. % polyethylene glycol (PEG) and 45 wt. % butyleneterephthalate (PBT), the PEG having an average molecular weight of 1000 kD) were combined in a solvent of chloroform in the proportions shown below in Table 12 in order to form a series of combination degradable/non-degradable polymer solutions.

TABLE 12

| Combination Polymer Solution Number | pBMA (mg/ml) | pEVA (mg/ml) | 1000PEG55 (mg/ml) | Total Solids (mg/ml) |
| --- | --- | --- | --- | --- |
| A | 6.25 mg/ml | 6.25 mg/ml | 12.5 mg/ml | 25 mg/ml |
| B | 3.125 mg/ml | 3.125 mg/ml | 18.75 mg/ml | 25 mg/ml |

Non-specific rabbit Fab fragments were obtained from Southern Biotech (Birmingham, Ala.). The Fab fragments were desalted using 4 desalting columns (Econo-Pac 10 DG, Bio-Rad, Hercules, Calif.). 5 mM PBS was prepared without NaCl (pH=7.31). 20 ml of the 5 mM PBS was then put on each of the 4 columns. 2.5 ml of a Fab fragment solution (A280 (50 μl)=0.898, ε=1.35) with a Fab concentration of 13.3 mg/ml, was put on each column and allowed to absorb completely. The columns were then filled completely with the 5 mM PBS solution. Elution samples were collected of approximately 1 ml each and analyzed with a spectrophotometer (SpectraMax M2, Molecular Devices) for absorbance at a wavelength of 280 nm ("A280"). The Fab fragment concentration was increased using centrifuge filters (10 kDa cutoff, Pall Corporation, East Hills, N.Y.) filled with 3.5 ml protein solution and spun at 5500 g for various amounts of time at 6 degrees Celsius. Fab fragment solutions ("active agent solutions") of 21.4 mg/ml ("solution C") and 10 mg/ml ("solution D") were thus obtained (concentration based on A280 measurements).

MP-35N alloy coils (n=4 per group) were used as a substrate. First, the base coat solution described above was applied to all of the coils with a spray system from a single ultrasonic spray nozzle (60 KHz ultrasonic nozzle from Sono-Tek, Milton, N.Y. operating at about 0.5 to 1.5 watts) in an amount of between about 100 μg and 200 μg (equal parts pEVA and pBMA) solids.

Next, the combination degradable/non-degradable polymer solutions and active agent solutions were then applied to the alloy coils with an ultrasonic spray system from two ultrasonic spray heads (60 KHz ultrasonic nozzles from Sono-Tek, Milton, N.Y. operating at about 0.5 to 1.5 watts). The combination degradable/non-degradable polymer solution was applied from one spray head while the active agent solution was simultaneously applied from the other spray head. The specific flow rates and solutions used are identified below in Table 13.

TABLE 13

| Coil Number | Degradable/ Nondegradable Polymer Solution | Flow Rate (ml/min) | Active Agent Solution | Flow Rate (ml/min) |
| --- | --- | --- | --- | --- |
| 1 | A | 0.047 | C | 0.02 |
| 2 | A | 0.0988 | C | 0.02 |
| 3 | B | 0.0324 | C | 0.02 |
| 4 | B | 0.0637 | C | 0.02 |
| 5 | A | 0.07 | D | 0.015 |
| 6 | B | 0.016 | D | 0.02 |
| 7 | A | 0.016 | D | 0.02 |
| 8 | B | 0.065 | D | 0.02 |

The coated coils included the ratios of components (pEVA: pBMA:1000PEG55:Fab) as shown below in Table 14. The coating weight was determined by comparing the weight of the coil before and after application (after drying) of the combination degradable/nondegradable polymer solution and the active agent solution.

TABLE 14

| Coil Number | pEVA:pBMA:1000PEG55:Fab | Coating Weight (ug) | % Protein Load |
|---|---|---|---|
| 1 | 1:1:3:2 | 800 | 25% |
| 2 | 3:3:6:2 | 1408 | 14.28% |
| 3 | 1:1:6:4 | 606 | 33% |
| 4 | 1:1:6:2 | 1000 | 20% |
| 5 | 3:3:6:1 | 2600 | 8% |
| 6 | 1:1:6:6 | 467 | 43% |
| 7 | 1:1:2:2 | 606 | 33% |
| 8 | 1:1:6:1 | 1800 | 11% |

A top coat of parylene was then applied to coil numbers 4 and 5. Specifically a 1 gram charge of parylene-C dimer was deposited over each of coil numbers 4 and 5 using a standard vapor deposition process.

Figure 11:
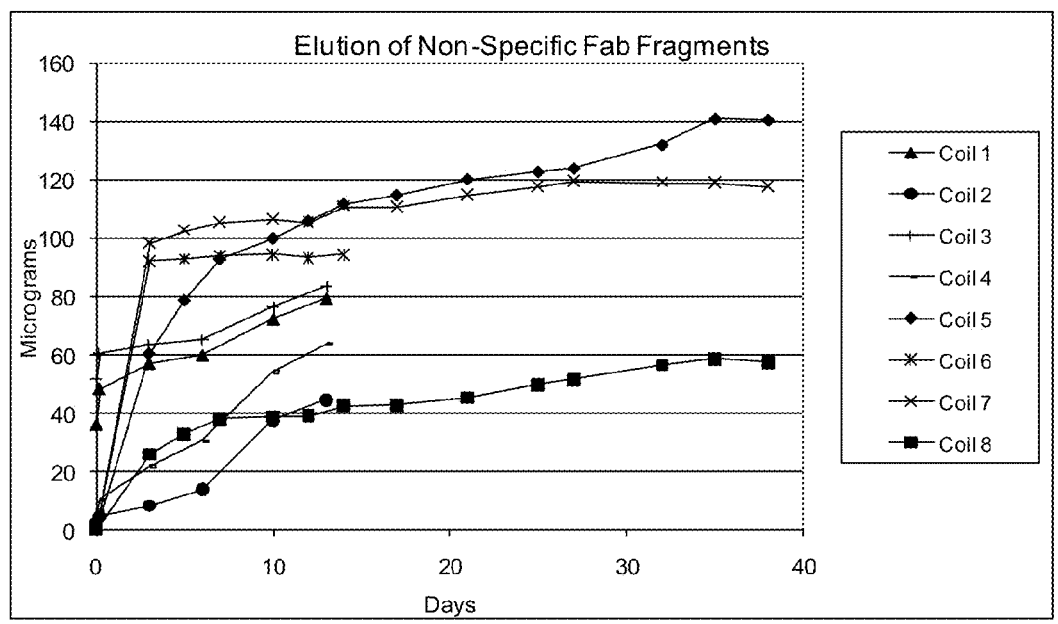
FIG. 11 is a graph showing the elution of nonspecific Fab fragments from a various coatings in accordance with various embodiments of the invention.

Release of the Fab fragments from the combination degradable/nondegradable coatings was then assessed. Specifically, the coils were placed in a solution of PBS held at 37 degrees Celsius. The solution was replaced at various time points. The concentration of Fab fragments in the solution samples was then assessed using a tryptophan fluorescence assay. Specifically, the solution samples were first denatured at room temperature by adding an equal volume of 12M guanidine solution (150 ul sample+150 ul 12 M guanidine HCl in distilled deionized water in black 96-well-plate) The 96-well plate was then incubated at −20 degrees Celsius for 10 minutes. Fluorescence was read using a spectrophotometer (SpectraMax M2, Molecular Devices) at $\lambda_{ex}$=290 nm and $\lambda_{em}$=370 nm. The tryptophan assay results are shown in FIG. 11.

Example 9

Release of Fab Fragment Particles from Degradable/Non-Degradable Matrix on Coil Substrate Protein Preparation:

5 mM PBS was prepared without NaCl (pH=7.31). 20 ml of the 5 mM PBS was then put on each of 4 Bio-Rad columns (Econo-Pac 10 DG, Bio-Rad, Hercules, Calif.). 2.5 ml of a Fab fragment (rabbit anti-goat, Southern Biotech, Birmingham, Ala.) solution (A280 (50 µl)=0.898, ε=1.35) with a Fab concentration of 13.3 mg/ml, was put on each column and allowed to absorb completely. The columns were then filled completely with the 5 mM PBS solution. Elution samples were collected of approximately 1 ml each and analyzed with a spectrophotometer (SpectraMax M2, Molecular Devices) for absorbance at a wavelength of 280 nm ("A280"). The first 4 fractions of all 4 columns were combined (~19 ml, A280=0.491) and found to have a concentration of Fab fragments of 7.27 mg/ml.

2 centrifuge filters (10 kDa cutoff, Pall Corporation, East Hills, N.Y.) were filled with 3.5 ml protein solution (first 4 fractions of each column) and spun at 5500 g for 50 minutes at 6 degrees Celsius. To the remaining supernatant, 3 ml of the remaining solution was added and spun under same conditions for 50 minutes. The supernatants were combined and added to the remaining solution (6 ml in total) forming a protein solution, and the absorbance was measured at 280 nm using a spectrophotometer (SpectraMax M2, Molecular Devices) (A280 (50 µl)=1.452, concentration=21.51 mg/ml or approximately 130 mg Fab in total).

Particle Formation:

The protein solution was held at 37 degrees Celsius for 10 minutes in a 50 ml centrifuge tube (VWR). A hole was pierced in the screw-cap. 8.67 ml of a 30% w/v polyethyleneglycol (PEG) (20 kDa Mw) solution (20 times w/w protein), preheated to 37 degrees Celsius, was added to the protein solution through the hole in the cap while vortexing. A white suspension was formed and poured into a plastic Petri-dish. The dish was covered and held consecutively at 4 degrees Celsius for 1 hour, at −20 degrees Celsius for 1 hour, and on dry ice for 30 minutes. The initially glossy appearance of the PEG/protein suspension became matte and solid. The frozen suspension was put in a vacuum oven for lyophilization at room temperature over night (vacuum 30 mm Hg).

PEG Extraction:

Once no soft or moist spots were noticed the dry cake was transferred to a 50 ml centrifuge tube and placed at −20 degrees Celsius for 2.5 days. 20 ml of HPLC grade chloroform was then added. The PEG dissolved rendering a cloudy fine protein suspension. The chloroform was dispensed into two 15 ml tubes and centrifuged at 5000 rpm and 4 degrees Celsius for 10 minutes. Using glass pipettes the chloroform was aspirated and stored. Fresh chloroform (10 ml per tube) was added. This washing procedure was done 3 times in total. The protein particles were then combined in 10 ml of chloroform and spun at 5000 rpm for 10 minutes at 4 degrees Celsius. The chloroform was aspirated off and protein particles were resuspended in 10 ml chloroform. The remaining protein from aspirated chloroform fractions was retrieved separately, washed 2 times and added to the main batch.

The suspension was homogenized with a hand-held homogenizer operating at 21 krpm and subsequently filtered through a 20 µm polypropylene filter (Buchner filter). All Fab particles passed through the filter. The filtered batch was collected in a 20 ml boronated glass vial.

The concentration of the Fab particle suspension was then measured in duplicate. Specifically, 50 µl of the suspension was dispensed on a glass cover slip and weighed. The cover slip was then placed in a plastic Petri-dish and washed with 1 ml of 5 mM PBS. The PBS solution was then analyzed for protein concentration using a spectrophotometer (SpectraMax M2, Molecular Devices) by assessing absorbance at 280 nm. The weighed amount was compared to the number calculated from the data obtained from the spectrophotometer at A280. Those values were comparable. Differences in values were believed to result from the presence of residual PEG. The results are shown in Table 15 below. 200 µl was sampled and stored at 4 degrees Celsius.

TABLE 15

| Sample | Total Solids (as weighed) | Solids Concentration | Absorbance at 280 nm | Fab Concentration |
|---|---|---|---|---|
| 1 | 0.311 mg | 6.22 mg/ml | 0.349 | 5.17 mg/ml |
| 2 | 0.302 mg | 6.04 mg/ml | 0.340 | 5.03 mg/ml |

A combination degradable/non-degradable/active agent coating solution was then prepared. Specifically, 14 ml of the Fab particle suspension (containing 72.38 mg Fab particles) was transferred to a clean boronated glass vial. Then, 36.19 mg of 1000PEG45 (45 wt. % polyethylene glycol (PEG, average molecular weight of 1000 kd) and 55 wt. % butyleneterephthalate (PBT)) was added to the glass vial. The mixture was shaken until all components were observed to be dissolved. The mixture was then held at −20 degrees Celsius over night. Next, 66.6 mg of poly-n-butylmethacrylate (PBMA) and 66.6 mg of polyethylene-co-vinyl acetate (pEVA) were added. The mixture was shaken at 32 degrees Celsius for 60 minutes prior to coating.

MP35N alloy coils were used as the coating substrate. The coating solution was then applied to the alloy coils with an ultrasonic spray system with a single ultrasonic spray head (60 KHz ultrasonic nozzles from Sono-Tek, Milton, N.Y. operating at about 0.5 to 1.5 watts). The coils were allowed to dry overnight.

Figure 12:
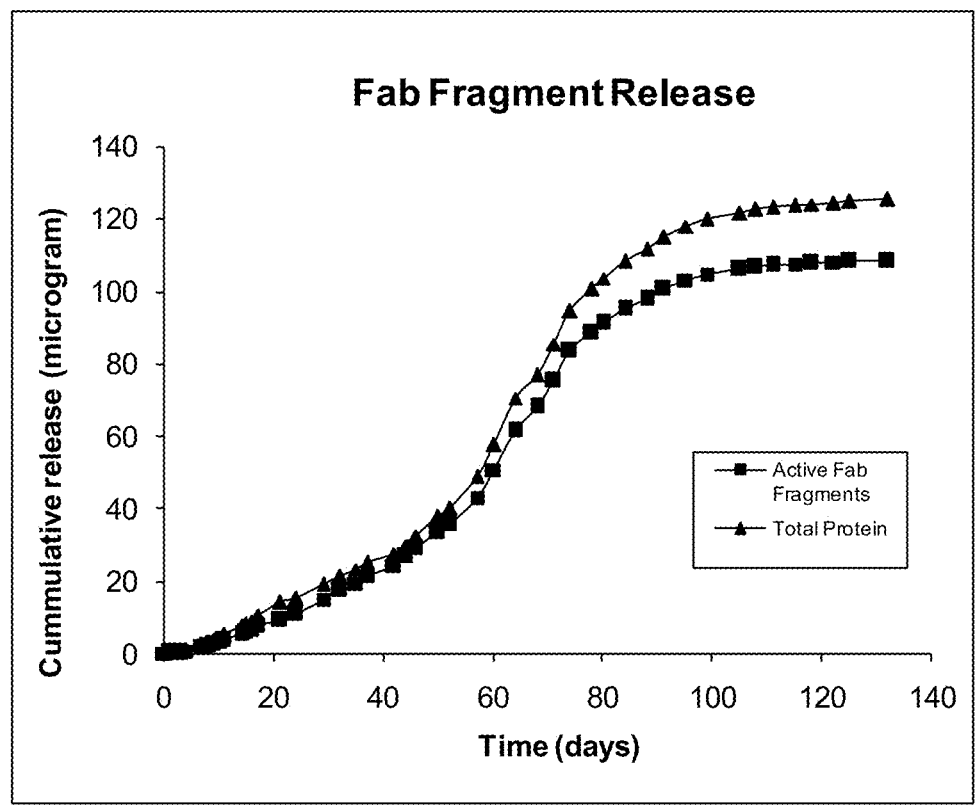
FIG. 12 is a graph showing the elution of Fab fragments from various coatings in accordance with various embodiments of the invention.
Figure 13:
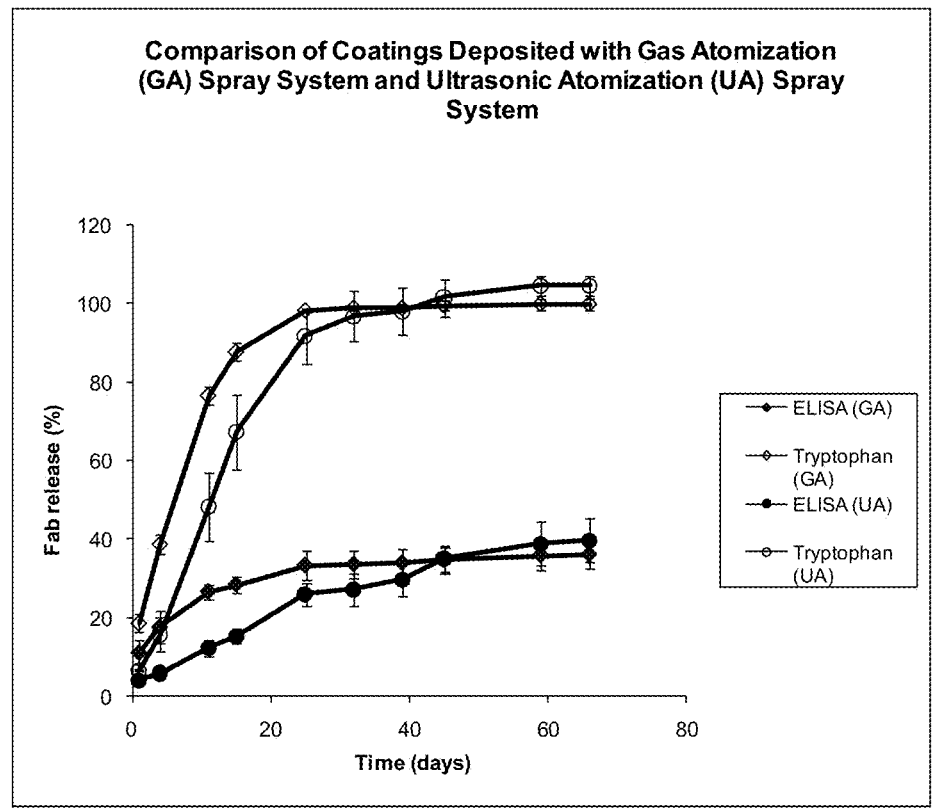
FIG. 13 is a graph showing the elution of Fab fragments from various coatings in accordance with various embodiments of the invention.

Release of the Fab fragments from the combination degradable/nondegradable coatings was then assessed. Specifically, the coils were placed in a solution of PBS, and the solution was replaced at various time points. A tryptophan assay (total protein) was performed on the replaced solution samples. In the tryptophan assay, the solution samples (150 µl each) were first denatured at room temperature by adding an equal volume (150 µl) of 12M guanidine solution (12 M guanidine HCL in distilled deionized water) and then were incubated at −20 degrees Celsius for 10 minutes. Fluorescence was read using a spectrophotometer (SpectraMax M2, Molecular Devices) at $\lambda_{ex}$=290 nm and $\lambda_{em}$=370 nm. Activity of the Fab fragments was then assessed using an ELISA assay. The assay results are shown in FIG. 12.

Example 10

Release of Fab Fragment Particles from Degradable/Non-Degradable Matrix Deposited on Coil Substrate with Ultrasonic and Gas Atomization Coating Systems Protein Preparation:

5 mM PBS without NaCl was prepared from a 10×PBS stock solution. 25 ml was diluted in deionized water (18.1Ω) to a total volume of 500 ml. pH was adjusted to pH=7.31 after adding one drop of $H_3PO_4$.

4 Bio-Rad columns were prepared and the storage buffer was disposed. Columns were eluted with 20 ml 5 mM PBS. 2.5 ml of a Fab fragment solution (Rabbit anti-Goat) (Southern Biotech, Birmingham, Ala.), A280 (50 µl)=0.953, ε=1.35=>14.1 mg/ml, was put on each column and let be absorbed completely. The columns were then filled completely with 5 mM PBS. Elution samples were collected of approximately 1 ml each and analyzed with a spectrophotometer (Spectramax M2, Molecular Devices) to assess absorbance at 280 nm (A280). The first 4 fractions of two pairs of columns were combined (8.8 ml with a concentration of 7.08 mg/ml and 8.6 ml with a concentration of 6.12 mg/ml).

4 centrifuge filters (10 kDa cutoff, Pall Corporation, East Hills, N.Y.) were filled with 3 ml protein solution and spun at 5500 g for 50 minutes at 6 degrees Celsius. To the remaining supernatant the rest of the solution was added and spun under same conditions for 10 minutes. The supernatants were combined forming a protein solution (5.5 ml) (A280 (50 μl)=1.520, conc=22.52 mg/ml).

Particle Formation:

The protein solution was held at 37 degrees Celsius for 10 minutes in a 50 ml centrifuge tube (VWR). A hole was pierced in the screw-cap. 6.67 ml of a 30% w/v polyethyleneglycol “PEG” 20 kDa solution, pre-heated to 37 degrees Celsius, was added to the protein solution through the hole in the cap while vortexing. A white suspension was formed and poured in a plastic Petri-dish. The dish was covered and put consecutively at 4 degrees Celsius for 1 hour, at −20 degrees Celsius for 1.5 hour and on dry ice for 30 minutes. The initially glossy appearance of the PEG/protein suspension became matte and solid. The frozen suspension was put for lyophilization in a vacuum oven at room temperature over night (vacuum 30 mm Hg).

Once no soft spots were noticed the dry cake was transferred to a 50 ml centrifuge tube. 20 ml of HPLC grade chloroform was added. The PEG dissolved rendering a cloudy fine protein suspension. The chloroform was dispensed in two 15 ml tubes and centrifuged at 5000 rpm at 4 degrees Celsius for 10 minutes. Using glass pipettes the chloroform was aspirated and stored. Fresh chloroform (10 ml per tube) was added. This washing procedure was done 3 times in total. The protein particles were resuspended in 10 ml chloroform. Remaining protein from aspirated chloroform fractions was retrieved separately, washed 2 times and added to the main batch.

The suspension was subsequently filtered through a 20 μm polypropylene filter (Buchner filter) and collected in a 20 ml boronated glass vial. The concentration was measured in triplicate. Specifically, 50 μl of the suspension was dispensed on a glass cover slip and weighed. The cover slip was placed in a plastic Petri-dish and washed with 1 ml of 5 mM PBS. The PBS was analyzed for protein concentration using a spectrophotometer to measure absorbance at 280 nm (A280). 200 μl was sampled and stored at 4 degrees Celsius.

Spray Coating:

Then a combination degradable/non-degradable coating solution was prepared. First, the particles as prepared above were suspended in chloroform at 5 mg/ml concentration. 5 ml of the Fab particle suspension (containing 25 mg Fab particles) was then transferred to a clean boronated glass vial. Then, 12.5 mg of 1000PEG45 (45 wt. % polyethylene glycol (PEG, average molecular weight of 1000 kd) and 55 wt. % butyleneterephthalate (PBT)) was added to the glass vial. The mixture was shaken until all components were observed to be dissolved. The mixture was then held at −20 degrees Celsius over night. Next, 23 mg of poly-n-butylmethacrylate (pBMA) and 23 mg of polyethylene-co-vinyl acetate (pEVA) were added. The mixture was shaken at 32 degrees Celsius for 60 minutes prior to coating. The resulting coating solution included 30 wt. % Fab particles, 15 wt. % 1000PEG45, 27.5% pBMA, and 27.5% pEVA, of total solids.

MP35N alloy coils (n=8) were used as the coating substrate. Four coils were spray coated using a spray coating apparatus with a gas atomization nozzle. Four coils were spray coated using a spray coating apparatus with an ultrasonic nozzle (60 KHz ultrasonic nozzle from Sono-Tek, Milton, N.Y. operating at about 0.5 to 1.5 watts). The alloy coils were weighed before and after coating. The coils were stored at 4 degrees Celsius.

Release of the Fab fragments from the combination degradable/nondegradable coatings was then assessed. Specifically, the coils were placed in a solution of PBS, and the solution was replaced at various time points. A tryptophan assay was performed on the replaced solution samples. In the tryptophan assay, the solution samples (150 μl each) were first denatured at room temperature by adding an equal volume (150 μl) of 12M guanidine solution (12 M guanidine HCL in distilled deionized water) and then were incubated at −20 degrees Celsius for 10 minutes. Fluorescence was read using a spectrophotometer (SpectraMax M2, Molecular Devices) at $\lambda_{ex}$=290 nm and $\lambda_{em}$=370 nm. Activity of the Fab fragments was then assessed using an ELISA assay. The assay results are shown in FIG. 13.

Example 11

Release of Fab Fragment Particles from Degradable/Non-Degradable Matrices with Varying Degradable/Non-Degradable Ratios Protein Preparation:

5 mM PBS (phosphate buffered saline) without NaCl was prepared from a 10×PBS stock solution. 25 ml was diluted in deionized water (18.1Ω) to a total volume of 500 ml. The pH was adjusted to pH=7.31 after adding one drop of $H_3PO_4$.

4 Bio-Rad columns (Econo-Pac 10DG, Bio-Rad, Hercules, Calif.) were prepared. 20 ml of 5 mM PBS solution was put onto the columns. 2.5 ml of Fab fragments (rabbit anti-goat) (Southern Biotech, Birmingham, Ala.), (A280 (50 µl)=0.953, ε=1.35) with a concentration of 14.1 mg/ml, was put onto each column and allowed to absorb completely. The columns were then filled completely with 5 mM PBS. Elution samples were collected of approximately 1 ml each and analyzed using a spectrophotometer and assessing the absorbance at 280 nm. The first 4 fractions of two pairs of columns were combined (8.8 ml with a concentration of 7.08 mg/ml Fab and 8.6 ml with a concentration of 6.12 mg/ml Fab).

4 centrifuge filters (10 kDa cutoff, Microsep 10K Omega, Pall Corporation, East Hills, N.Y.) were filled with 3 ml protein solution and spun at 5500 g for 50 minutes at 6 degrees Celsius. To the remaining supernatant the rest of the solution was added and spun under same conditions for 10 minutes. The supernatants were combined (5.5 ml, A280 (50 µl)=1.520, conc=22.52 mg/ml).

Particle Preparation:

The protein solution was held at 37 degrees Celsius for 10 minutes in a 50 ml centrifuge tube (VWR). A hole was pierced in the screw-cap. 6.67 ml of a 30% w/v polyethyleneglycol (PEG) (m.w.=20 kDa) solution, pre-heated to 37 degrees Celsius, was added to the protein solution through the hole in the cap while vortexing. A white suspension was formed and poured into a plastic Petri-dish. The dish was covered and put consecutively at 4 degrees Celsius for 1 hour, at −20 degrees Celsius for 1.5 hour and on dry ice for 30 minutes. The initially glossy appearance of the PEG/protein suspension became matte and solid. The frozen suspension was put for lyophilization in a vacuum oven at room temperature over night (vacuum 30 mm Hg).

Once no soft spots were noticed, the dry cake was transferred to a 50 ml centrifuge tube. 20 ml of HPLC grade chloroform was added. The PEG dissolved rendering a cloudy fine protein suspension. The chloroform was dispensed into two 15 ml tubes and centrifuged at 5000 rpm, at 4 degrees Celsius for 10 minutes. Using glass pipettes the chloroform was aspirated and stored. Fresh chloroform (10 ml per tube) was added. This washing procedure was done 3 times in total. The protein particles were resuspended in 10 ml chloroform. Remaining protein from the aspirated chloroform fractions was retrieved separately, washed two times and added to the main batch.

The suspension was subsequently filtered through a 20 µm polypropylene filter (Buchner filter) and collected in a 20 ml boronated glass vial. The concentration was measured in triplicate. Specifically, 50 µl of the suspension was dispensed on a glass cover slip and weighed. The cover slip was placed in a plastic Petri-dish and washed with 1 ml of 5 mM PBS. The PBS was analyzed for protein concentration using a spectrophotometer and measuring absorbance at 280 nm (A280). The concentration was found to be 11.8 mg/mL based on solids and 11.9 mg/mL based on A280 (A280=0.802, 0.594 mg for 50 µl). 200 µl was sampled and stored at 4 degrees Celsius.

Coating Solutions:

Four different combination degradable/nondegradable coating solutions were prepared. Specifically, poly-n-butyl-methacrylate (pBMA), polyethylene-co-vinyl acetate (pEVA), poly(butyleneterephthalate-co-ethylene glycol) ("degradable"), and Fab particles were combined in a solvent of chloroform in order to form the four different coating solutions. Each solution had a ratio of pBMA:pEVA:poly (butyleneterephthalate-co-ethylene glycol):Fab equal to 1.85:1.85:1:2. Total solids concentration was kept at 4.5 mg/ml, with Fab particles being 3 mg/ml. The difference between the coating solutions was the ratios of two different types of poly(butyleneterephthalate-co-ethylene glycol): 1.) ("1000PEG55") (55 wt. % polyethylene glycol (PEG, m.w. 1000 kd) and 45 wt. % butyleneterephthalate (PBT); and 2.) ("1000PEG80") (80 wt. % polyethylene glycol (PEG, m.w. 1000 kd) and 20 wt. % butyleneterephthalate (PBT). The relative amounts of 1000PEG55 and 1000PEG80 for each coating solution are shown below in Table 16.

TABLE 16

| Coating Solution | 1000PEG80 | 1000PEG55 |
|---|---|---|
| 1 | 100% | 0% |
| 2 | 80% | 20% |
| 3 | 50% | 50% |
| 4 | 20% | 80% |

MP35N alloy coils were used as the substrate. Each coil was weighed. The coating solutions were applied on to 3 coils per group using a spray coating apparatus with a single ultrasonic spray nozzle (60 KHz ultrasonic nozzle from Sono-Tek, Milton, N.Y. operating at about 0.5 to 1.5 watts). After coating, the coils were allowed to dry overnight and then weighed again. The total amount of solids deposited on each coil was roughly 1000 µg. The total amount of fab fragments deposited on each coil was approximately 300 µg.

Figure 14:
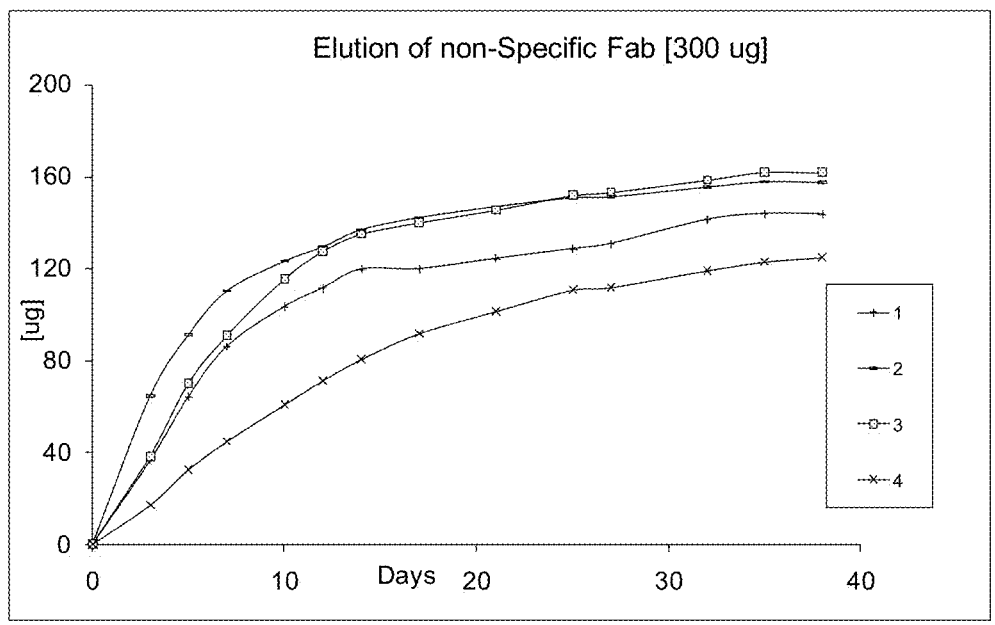
FIG. 14 is a graph showing the elution of nonspecific Fab fragments from various coatings in accordance with various embodiments of the invention.

Release of the Fab fragments from the combination degradable/nondegradable coatings was then assessed using a tryptophan assay. Specifically, the coils were placed in a solution of PBS held at 37 degrees Celsius. The solution was replaced at various time points. The concentration of Fab fragments in the solution samples was the assessed using a tryptophan fluorescence assay. Specifically, the solution samples (150 µl) were first denatured at room temperature by adding an equal volume (150 µl) of 12M guanidine solution (12 M guanidine HCL in distilled deionized water) and then were incubated at −20 degrees Celsius for 10 minutes. Fluorescence was read using a spectrophotometer (SpectraMax M2, Molecular Devices) at $\lambda_{ex}$=290 nm and $\lambda_{em}$=370 nm. Cumulative elution of non-specific Fab fragments, as assessed by the tryptophan assay, are shown in FIG. 14.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A method of making an active agent delivery matrix comprising:
   mixing a degradable polymer with a first polar solvent to form a degradable polymer solution;
   mixing a non-degradable polymer with a second non-polar solvent that is immiscible with the first polar solvent to form a non-degradable polymer solution, wherein the non-degradable polymer comprises a first polymer component comprising a polymer selected from poly(alkyl (meth)acrylate), poly(aromatic(meth)acrylate), and combinations thereof and a second polymer component comprising poly(ethylene-co-vinyl acetate); and
   simultaneously depositing the degradable polymer solution onto a substrate by spraying the degradable polymer solution from a first spray nozzle while simultaneously spraying the non-degradable polymer solution onto the substrate from a second spray nozzle to form an active agent delivery matrix in which the degradable polymer network and the non-degradable polymer network form an interpenetrating matrix, wherein the active agent delivery matrix comprises from 15 wt. % to 50 wt. % degradable polymer and from about 20 wt % to about 60 wt % non-degradable polymer.

2. The method of claim 1, further comprising mixing an active agent in with the non-degradable polymer solution.

3. The method of claim 1, further comprising mixing an active agent in with the degradable polymer solution.

* * * * *

UNITED STATES PATENT AND TRADEMARK OFFICE
CERTIFICATE OF CORRECTION

PATENT NO.        : 8,968,782 B2  
APPLICATION NO.   : 11/770316  
DATED             : March 3, 2015  
INVENTOR(S)       : Ralph A. Chappa et al.

Page 1 of 1

It is certified that error appears in the above-identified patent and that said Letters Patent is hereby corrected as shown below:

On the Title Page, item 57, line 1, in the abstract -- "invention relates to relates to combination" should read --invention relates to combination--

Signed and Sealed this
Twenty-fifth Day of August, 2015

Michelle K. Lee
*Director of the United States Patent and Trademark Office*